(12) United States Patent
Shimodaira

(10) Patent No.: US 9,341,579 B2
(45) Date of Patent: May 17, 2016

(54) DEFECT DETECTION APPARATUS, DEFECT DETECTION METHOD, AND COMPUTER PROGRAM

(75) Inventor: Masato Shimodaira, Osaka (JP)

(73) Assignee: Keyence Corporation, Osaka (JP)

( * ) Notice: Subject to any disclaimer, the term of this patent is extended or adjusted under 35 U.S.C. 154(b) by 905 days.

(21) Appl. No.: 13/352,427

(22) Filed: Jan. 18, 2012

(65) Prior Publication Data

US 2012/0206593 A1 Aug. 16, 2012

(30) Foreign Application Priority Data

Feb. 14, 2011 (JP) ................................. 2011-029066

(51) Int. Cl.
*H04N 7/18* (2006.01)
*G01N 21/88* (2006.01)

(52) U.S. Cl.
CPC ............. *G01N 21/8851* (2013.01); *H04N 7/18* (2013.01); *G01N 2021/8874* (2013.01)

(58) Field of Classification Search
CPC ............................. H04N 7/18; G01N 21/8851
USPC ........................................................ 348/125
See application file for complete search history.

(56) References Cited

U.S. PATENT DOCUMENTS

| 5,287,290 | A * | 2/1994 | Tabara ................ G06F 17/5081 250/491.1 |
| 6,222,935 | B1 * | 4/2001 | Okamoto ......... G01N 21/95607 382/147 |
| 8,014,628 | B2 | 9/2011 | Shimodaira |
| 8,086,024 | B2 | 12/2011 | Shimodaira |
| 2002/0019729 | A1 * | 2/2002 | Chang ....................... G03F 1/26 703/6 |
| 2007/0019808 | A1 * | 1/2007 | Gonzalez ............. G06K 9/6211 380/51 |
| 2008/0310694 | A1 * | 12/2008 | Nozaki ................ G06K 9/6206 382/130 |
| 2009/0202135 | A1 * | 8/2009 | Shimodaira .......... G06K 9/6204 382/141 |
| 2009/0208050 | A1 * | 8/2009 | Shimodaira ............. G06T 5/005 382/100 |
| 2010/0177347 | A1 * | 7/2010 | Mitani .................. G06F 3/1204 358/1.15 |
| 2011/0019933 | A1 * | 1/2011 | Noda ....................... G06K 9/40 382/260 |
| 2013/0101233 | A1 * | 4/2013 | Noda ....................... G06K 9/40 382/275 |

FOREIGN PATENT DOCUMENTS

| JP | 2004-108845 | 4/2004 |
| JP | 2006-050356 | 2/2006 |
| JP | 2009-199126 | 9/2009 |
| JP | 2011-028588 | 2/2011 |

* cited by examiner

*Primary Examiner* — Richard Torrente
*Assistant Examiner* — Irfan Habib
(74) *Attorney, Agent, or Firm* — Kilyk & Bowersox, P.L.L.C.

(57) ABSTRACT

The present invention provides a defect detection apparatus for detecting a defect even on a uniformly continuous background pattern, a method used in the apparatus, and a computer program for making a computer execute processing in the method. A defect size is set and stored, and an instruction to a first direction in which a background pattern is uniformly continuous is accepted. A reduced image reduced in the first direction using an image reduction ratio according to the defect size is generated. A filter processing is executed in the first direction for removing a defect, and the reduced image that is subjected to the filter processing is enlarged in the first direction with an image enlargement ratio corresponding to the reciprocal of the reduction ratio to generate a first enlarged image. A difference image is generated by calculating a difference between the multi-valued image and the first enlarged image.

20 Claims, 12 Drawing Sheets

DEFECT DETECTION APPARATUS, DEFECT DETECTION METHOD, AND COMPUTER PROGRAM

CROSS-REFERENCE TO RELATED APPLICATIONS

The present application claims foreign priority based on Japanese Patent Application No. 2011-029066, filed Feb. 14, 2011, the contents of which is incorporated herein by reference.

BACKGROUND OF THE INVENTION

1. Field of the Invention

The present invention relates to a defect detection apparatus for detecting a defect such as dust, a flaw, or dirt on a uniformly continuous background pattern of a multi-valued image acquired by capturing an image of an object surface, a defect detection method used in the defect detection apparatus, and a computer program for making a computer execute processing in the defect detection method.

2. Description of Related Art

As a conventional example, a scanning apparatus has been proposed in which an n-order approximation is performed by adopting a least square method on each line in an original image which was acquired by imaging with a digital camera and includes shading and a singular point formed by a defect such as dust, a flaw or dirt. Data from all lines are integrated to generate shading image data as flattened data, a difference between the original image data and the shading image data is calculated, and when the difference indicates a singular point that is larger than a prescribed value, the singular point is determined to be a singular point due to a defect (refer to e.g. Japanese Patent Application Laid-Open No. 2006-050356).

However, in the conventional example above, when non-periodic complex shading is generated, a user will encounter difficulty when setting an appropriate order n of an n-order approximate curve for detecting a defect, and even when a shading image is generated by using a large setting for the order n, the shading image will not match the original image. Hence there is a problem in that an approximate error occurs in the inconsistent portion and a difference due to the approximation error cannot be distinguished from a difference due to a defect portion.

In this context, Japanese Patent Application Laid-Open No. 2009-199126 discloses a defect detection apparatus that enables highly accurate detection of a defect that is no larger than a size determined by a user based on a difference image between an original multi-valued image and an enlarged image by removing defect images that are not greater than a set size from a reduced image.

CITATION LIST

Patent Literature

[Patent Literature 1] Japanese Patent Application Laid-Open No. 2006-050356
[Patent Literature 2] Japanese Patent Application Laid-Open No. 2009-199126

SUMMARY OF THE INVENTION

In the above conventional examples, although non-periodic complex shading can be eliminated, when the background pattern is uniformly continuous, for example, when a striped background pattern is generated, although the shading can be eliminated, the problem arises that the striped pattern cannot be eliminated and therefore remains. Consequently, difficulties arise in relation to the correct detection of a defect such as dust, a flaw or dirt.

The present invention has been made in view of the above problems, and an object thereof is to provide a defect detection apparatus capable of highly accurate detection of a defect such as dust, a flaw or dirt even when the background pattern is uniformly continuous, a defect detection method used in the defect detection apparatus, and a computer program for making a computer execute processing in the defect detection method.

In order to achieve the above object, a defect detection apparatus according to a first aspect of the invention is a defect detection apparatus for detecting a defect on an imaged object surface from a multi-valued image captured by an imaging device, and has a configuration including: a size setting and accepting device for accepting a setting of a size of a defect as a detection object; a size storing device for storing a size of a defect for which a setting has been accepted by the size setting accepting device; a direction instruction accepting device for accepting an instruction in relation to a first direction in which a background pattern is uniformly continuous; a direction storing device for storing the first direction for which an instruction has been accepted in the direction instruction accepting device; an image reducing device for generating a reduced image obtained by reducing the multi-valued image in the stored first direction using an image reduction ratio according to the size of the stored defect; a filter processing device for performing filter processing in the first direction on the reduced image for removing a defect in the reduced image; an image enlarging device for generating a first enlarged image obtained by enlarging the reduced image, subjected to the filter processing by the filter processing device, in the first direction with an image enlargement ratio corresponding to the reciprocal of the image reduction ratio; and a difference calculating device for generating a difference image by calculating a difference between the multi-valued image and the first enlarged image.

It is preferred that the defect detection apparatus according to a second aspect of the invention includes the first aspect, and includes a noise reduction degree setting accepting device for accepting a setting of a noise reduction degree in relation to the difference image generated by the difference calculating device, and a noise reduction processing device for adding or subtracting the accepted noise reduction degree to or from the difference image to thereby generate a noise reduction processing image.

It is preferred that the defect detection apparatus according to a third aspect of the invention includes the first aspect or the second aspect, and includes a gain setting accepting device for accepting a setting of a gain in relation to the difference image, and a highlighting processing device for multiplying the accepted gain by the difference image to thereby generate a highlighting processing image.

It is preferred that the defect detection apparatus according to a fourth aspect of the invention includes any one of the first aspect to the third aspect, and the difference calculating device generates a positive difference image and a negative difference image, and a difference image selection accepting device is provided for accepting a selection of at least one of the positive difference image and the negative difference image, and a difference image selecting device is provided for selecting the accepted difference image.

It is preferred that the defect detection apparatus according to a fifth aspect of the invention includes any one of the first aspect to the fourth aspect, and the filter processing device is adapted to execute a setting so that the setting of a filter size or a number of times of passage through the filter increases as the size of the defect set by the size setting device increases.

It is preferred that the defect detection apparatus according to a sixth aspect of the invention includes any one of the first aspect to the fifth aspect, and includes an edge information extracting device for extracting edge information of the background pattern, and a direction specifying device for specifying the first direction based on the extracted edge information.

It is preferred that the defect detection apparatus according to a seventh aspect of the invention includes the sixth aspect, and includes an image rotating device for rotating an image so that the specified first direction is the vertical direction or the horizontal direction.

It is preferred that the defect detection apparatus according to an eighth aspect of the invention includes any one of the first aspect to the seventh aspect, and the image reduction ratio is set to 1, and the filter processing device sets the filter size or the number of times of passage through the filter in response to the size of the defect set by the size setting device.

It is preferred that the defect detection apparatus according to a ninth aspect of the invention includes any one of the first aspect to the eighth aspect, and an instruction for a second direction, that is a different direction from the first direction, is accepted by the direction instruction accepting device, and the direction storing device also stores the second direction for which the instruction has been accepted by the direction instruction accepting device, the image reducing device generates a reduced image in which the difference image of the first enlarged image and the multi-valued image is reduced in the second direction using the image reduction ratio, the filter processing device executes a filter processing in the second direction for removing a defect from the reduced image, the image enlarging device produces a second enlarged image in the second direction by enlarging the reduced image, that is subjected to filter processing, with an image enlargement ratio that corresponds to the reciprocal of the image reduction ratio, and the difference calculating device generates a second difference image by calculating the difference between the second enlarged image and the first difference image that is the difference image between the first enlarged image and the multi-valued image.

It is preferred that the defect detection apparatus according to a tenth aspect of the invention includes the ninth aspect, and the image reducing device generates a reduced image by reducing the multi-valued image in the second direction with the image reduction ratio, the filter processing device executes filter processing in the second direction to remove a defect from the reduced image, the image enlarging device produces a third enlarged image by enlarging the reduced image, that is subjected to filter processing, in the second direction with an image enlargement ratio that corresponds to the reciprocal of the image reduction ratio, and the difference calculating device generates a difference image by calculating the difference between the multi-valued image and a composite image that synthesizes the first enlarged image and the third enlarged image.

In order to achieve the above object, a defect detection method according to an eleventh aspect of the invention is a defect detection method used in the defect detection apparatus for detecting a defect on an imaged object surface from a multi-valued image captured by an imaging device, the method having a configuration such that setting of a size of a defect as a detection object is accepted; the size of a defect for which a setting has been accepted in the size setting accepting step is stored; an instruction in relation to a first direction in which a background pattern is uniformly continuous is accepted; a first direction for which an instruction has been accepted in the direction instruction accepting step is stored; a reduced image obtained by reducing the multi-valued image in the stored first direction using an image reduction ratio according to the size of the stored defect is generated; filter processing is executed in the first direction on the reduced image for removing a defect in the reduced image; a first enlarged image obtained by enlarging the reduced image, subjected to the filter processing in the filter processing step, in the first direction with an image enlargement ratio corresponding to the reciprocal of the image reduction ratio is generated; and a difference image obtained by calculating a difference between the multi-valued image and the first enlarged image is generated.

In order to achieve the above object, a computer program according to a twelfth aspect of the invention is a computer program that can be executed in the defect detection apparatus for detecting a defect on an imaged object surface from a multi-valued image captured by an imaging device, the computer program having a configuration of executing in the defect detection apparatus a size setting and accepting process for accepting a setting of a size of a defect as a detection object; a size storing process for storing a size of a defect for which a setting has been accepted by the size setting accepting device; a direction instruction accepting process for accepting an instruction in relation to a first direction in which a background pattern is uniformly continuous; a direction storage process for storing the first direction for which an instruction has been accepted in the direction instruction accepting process; an image reducing process for generating a reduced image obtained by reducing the multi-valued image in the stored first direction using an image reduction ratio according to the size of the stored defect; a filter process for performing filter processing in the first direction on the reduced image for removing a defect in the reduced image; an image enlarging process for generating a first enlarged image obtained by enlarging the reduced image, subjected to the filter processing by the filter processing device, in the first direction with an image enlargement ratio corresponding to the reciprocal of the image reduction ratio; and a difference calculating process for generating a difference image by calculating a difference between the multi-valued image and the first enlarged image.

In the first aspect, the eleventh aspect, and the twelfth aspect, a defect image no greater than the size set by a user is removed from the reduced image by reducing the multi-valued image only in the first direction in which the background pattern is uniformly continuous, executing a filter process, and enlarging to thereby generate a first enlarged image irrespective of a change or variation in the shading generation state contained in the multi-valued image acquired by image capture with an imaging device. Therefore the uniformly continuous background pattern can remain without being eliminated from the reduced image. Thus high accuracy detection of a defect no greater than a size determined by a user is enabled by use of a difference image between an original multi-valued image and the first enlarged image.

In the second aspect, reduction of noise from the difference image is enabled by a desired reduction degree set by a user by adding or subtracting the accepted noise reduction degree to or from the difference image to thereby generate a noise reduction processing image. Therefore, the accuracy of defect detection can be improved and visibility of the difference image can be improved.

In the third aspect, highlighting processing of the difference image is enabled by use of a desired gain set by a user by multiplying the accepted gain by the difference image to thereby generate a highlighting processing image. Therefore, the accuracy of defect detection can be further improved and visibility of the difference image can be improved.

In the fourth aspect, at least one of the difference images being the positive difference image exhibiting a bright defect image having a high luminosity value and the negative difference image exhibiting a dark defect image having a low luminosity value can be freely selected in relation to the luminosity value of the generated enlarged image (shading image), and thereby enables discrimination of a defect that is the detection object.

In the fifth aspect, suitable detection of a larger defect is enabled by increasing the setting of the filter size or a number of times of passage through the filter as the setting for the size of the defect increases.

In the sixth aspect, edge information for the background pattern is extracted, and the first direction is specified based on the extracted edge information to thereby enable tracking and detection of a defect even when there is a variation in the direction in which the background pattern is uniformly continuous.

In the seventh aspect, an image is rotated so that the specified first direction is the vertical direction or the horizontal direction to thereby reduce the calculation processing load and detect a defect with high accuracy without executing an image reducing process in relation to a direction of slope associated with a relatively high calculation processing load, a filtering process, or the like.

In the eighth aspect, the image reduction ratio is set to a value of 1, and the filter size or the number of times of passage through the filter is set in response to the set size of the defect to thereby inhibit extraction of contour portions of the detection object and enable detection of a defect without execution of an image reducing process.

In the ninth aspect, an instruction for a second direction, that is a different direction from the first direction, is accepted, a reduced image is generated in which the difference image of the first enlarged image and the multi-valued image is reduced in the second direction using the set image reduction ratio, filter processing is executed on the reduced image in the second direction for removing a defect from the reduced image, a second enlarged image is generated by enlarging the reduced image, subjected to filter processing, in the second direction with an image enlargement ratio that corresponds to the reciprocal of the image reduction ratio, and a second difference image is generated by calculating the difference between the second enlarged image and the first difference image that is the difference image between the first enlarged image and the multi-valued image. In this manner, high accuracy detection of a defect is enabled even when a background pattern is present that is uniformly continuous in two directions.

In the tenth aspect, a reduced image is generated by reducing the multi-valued image in the second direction with the set image reduction ratio, filter processing is executed on the reduced image in the second direction to remove a defect from the reduced image, a third enlarged image is generated by enlarging the reduced image, subjected to filter processing, in the second direction with an image enlargement ratio that corresponds to the reciprocal of the image reduction ratio, and a difference image is generated by calculating the difference between the multi-valued image and a composite image that synthesizes the first enlarged image and the third enlarged image. In this manner, a defect can be detected with enhanced accuracy while suppressing the calculation processing load even in relation to a multi-valued image containing a background pattern that is uniformly continuous in two directions.

According to the present invention, a defect image no greater than the size set by a user is removed from the reduced image by reducing the multi-valued image only in a first direction in which the background pattern is uniformly continuous, executing a filter process, and enlarging to thereby generate a first enlarged image, irrespective of a change or variation in the shading generation state contained in the multi-valued image acquired by capture with an imaging device. Therefore the uniformly continuous background pattern can remain without being eliminated from the reduced image. Thus high accuracy detection of a defect no greater than a size desired by a user is enabled by use of a difference image between an original multi-valued image and a first enlarged image.

DESCRIPTION OF THE PREFERRED EMBODIMENTS

Figure 1:
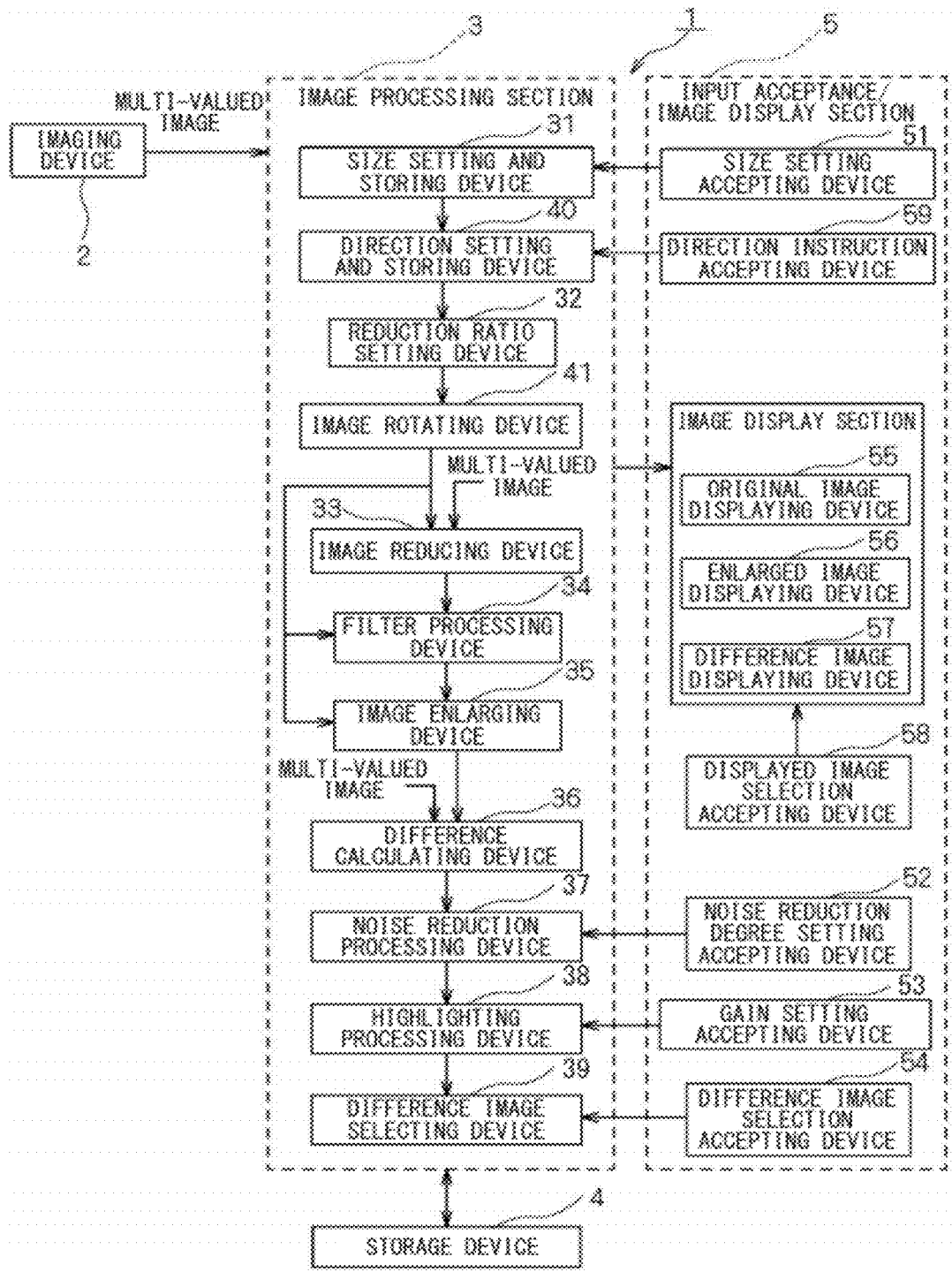
FIG. 1 is a block diagram showing an example of a schematic configuration of a defect detection apparatus according to a first embodiment of the present invention.

The embodiments of the present invention will be described in detail below with reference to the drawings. Those elements that have the same or similar configuration or function are denoted by the same or similar reference numerals in the figures referred to in the description of each embodiment, and such description will not be repeated.

Embodiment 1

FIG. 1 is a block diagram showing an example of a schematic configuration of a defect detection apparatus according to an embodiment of the present invention. As shown in FIG. 1, the defect detection apparatus 1 according to the first embodiment is configured from an imaging device 2, an image processing section 3, a storage device 4 and an input acceptance/image display section 5.

The imaging device 2 functions as a digital camera, for example, captures an image of a film surface, for example, as a detection object to thereby acquire a multi-valued image, and outputs the image to the image processing section 3.

The image processing section 3 includes a size setting and storing device 31, a reduction ratio setting device 32, an image reducing device 33, a filter processing device 34, an image enlarging device 35, a difference calculating device 36, a noise reduction processing device 37, a highlighting processing device 38, and a difference image selecting device 39, a direction setting and storing device 40, and an image rotating device 41. Further, the image processing section 3 is configured including a CPU, a ROM, a RAM, an external I/F, and the like, and controls processing operations of the size setting and storing device 31, the reduction ratio setting device 32, the image reducing device 33, the filter processing device 34, the image enlarging device 35, the difference calculating device 36, the noise reduction processing device 37, the highlighting processing device 38, the difference image selecting device 39, and the direction setting and storing device 40, and the image rotating device 41.

The storing device 4 functions as an image memory, and stores, as needed, an original multi-valued image captured by the imaging device 2 and an image after performance of each kind of processing in the image processing section 3. Furthermore, various types of set data is stored, and read out during execution of defect detection processing.

The input acceptance/image display section 5 is made up of a monitor, a mouse, a keyboard, and the like for a computer. The input acceptance section is provided, for example, on the display screen of the monitor as a dialog box, and includes a size setting accepting device 51, a noise reduction degree setting accepting device 52, a gain setting accepting device 53, a difference image selection accepting device 54, a displayed image selection accepting device 58, and a direction instruction accepting device 59. The image display section is provided adjacent to the input acceptance section on the display screen of the monitor, and includes an original image displaying device 55, an enlarged image displaying device 56, and a difference image displaying device 57. The user can select any of the original multi-valued image, the enlarged image, and the difference image in the displayed image selection accepting device 58 and display the selected image on the monitor screen.

Next, each configuration in the image processing section 3 will be described.

The size setting and storing device 31 stores a size of a defect that is accepted from the user by the size setting accepting device 51 of the input acceptance/image display section 5. As used herein, "defect size" indicates the number of pixels corresponding to the length when projected in a direction stored in the storing device 40. For example, it corresponds to the pixel number that corresponds to the width in the X direction when the X direction is stored, and to the height in the Y direction when the Y direction is stored.

The direction setting and storing device 40 accepts an instruction of the direction (first direction), in which the background pattern is uniformly continuous, in the direction instruction accepting device 59 of the input acceptance/image display section 5, and stores the direction of the accepted instruction as a direction for execution of the image reducing process, the filter process, and the image enlarging process.

The reduction ratio setting device 32 sets an image reduction ratio with respect to the original multi-valued image acquired by the imaging device 2, into the image reduction device 33 in accordance with the defect size set and stored by the size setting and storing device 31. The reduction ratio setting device 32 is configured, for example, in the form of a reference table of an image reduction ratio with a defect size taken as an argument such that the setting for the image reduction ratio increases (decreases) as the defect size increases (decreases).

The image reduction ratio is not necessarily calculated based upon the reference table, but may be calculated based upon a previously set defined calculation formula.

Further, the image reduction ratio described herein ranges from, for example, 1/2 to 1/50. The term "the image reduction ratio is large" as used herein is defined, for example, as 1/50 is a larger image reduction ratio than 1/2, whereas "to the contrary, the image reduction ratio is small" means that 1/2 is a smaller image reduction ratio than 1/50.

The image rotating device 41 rotates the image when the direction in which the background pattern is uniformly continuous (first direction) is inclined from the vertical direction or the horizontal direction, for example the X direction or the Y direction, so that the first direction becomes the vertical direction or the horizontal direction. In this manner, even when the direction in which the background pattern is uniformly continuous is inclined from the vertical direction or the horizontal direction, for example the X direction or the Y direction, the uniformly continuous background pattern can be removed without increasing the calculation load by executing the image reducing process, filter process, image enlarging process in relation to the X direction or the Y direction after the rotation operation.

The image reduction device 33 performs processing using, for example, a technique which is called an area square method, and reduces the original multi-valued image in the stored direction using the image reduction ratio set by the reduction ratio setting device 32 to generate a reduced image. As used herein, the area square method is a technique in which, for example, when reducing an original multi-valued image of 4.times.4 pixels into 1/4 in the X direction to generate a reduced image of 1.times.4 pixels, the original multi-valued image is divided into four blocks of 4.times.1 pixel, and a mean value of the intensity values of the four pixels constituting each block is calculated to generate a reduced image of 1.times.4 pixels with the mean value of each block taken as one pixel value.

When the original multi-value image of 4.times.4 pixels is reduced by 1/4 in the Y direction to generate a reduced image of 4.times.1 pixels, the original multi-value image is divided into 4 blocks of 1.times.4 pixels, and a mean value for the intensity value of the 4 pixels that configure each block is calculated, and the mean value of each block is taken as a 1 pixel value to thereby generate a reduced image of 4.times.1 pixels.

The filter processing device 34 functions as a secondary filter represented by a median filter, for example, and performs filter processing on the reduced image generated by the image reduction device 33 for removing a defect in the reduced image. The filter processing device 34 is configured including a reference table of a filter size (or the number of times of passage through the filter) with a defect size (or image reduction ratio) taken as an argument such that the setting for the filter size or the number of times of passage through the filter increases (decreases) as the defect size (or image reduction ratio) increases (decreases), and thereby a defect image that is no larger than a size set by a user is removed.

The image reduction ratio is not necessarily calculated based upon the reference table, but may be calculated based upon a previously set defined calculation formula.

As used herein, "filter size" indicates the number M of pixels configuring one side of two-dimensional filter of M.times.M pixels. Further, the median filter is a two-dimensional filter which substitutes a pixel value of a pixel under examination by a median value of pixel values of all pixels within a filter size range, and outputs the substituted value. In the first embodiment, since the filter process is executed in one direction, for example, when the filter process is executed in the X direction, the filter is extended in the transverse direction in M.times.1 pixels, and when the filter process is executed in the Y direction, the filter is extended in the vertical direction in 1.times.M pixels. The filter size means the value for M as described above.

The image enlarging device 35 performs processing, using a technique which is called a bilinear interpolation method, for example, and enlarges the reduced image, subjected to the filter processing in the stored direction by the filter processing device 34, at an image enlargement ratio corresponding to the reciprocal of the image reduction ratio, to thereby generate an enlarged image. The enlarged image corresponds to shading included in the original multi-valued image. As used herein, the bilinear interpolation method denotes an interpolation method in which linear interpolation is two-dimensionally enlarged and an interpolation value weighted and averaged in accordance with a distance from each of the four pixels around one pixel to the interpolation object pixel is taken as a pixel value of the interpolation object pixel. In the first embodiment, when executing image reduction in the X direction, interpolation may be performed only in the X direction, and when executing image reduction in the Y direction, interpolation may be performed only in the Y direction.

The difference calculating device 36 calculates a difference between the original multi-valued image and the enlarged image (first enlarged image) generated by the image enlarging device 35, to generate a difference image. The difference image is made up of a positive difference image showing a bright defect image with a high intensity value, and a negative difference image showing a dark defect image with a low intensity value with respect to a intensity value of the enlarged image (shading image) generated by the image enlarging device 35.

The noise reduction processing device 37 subtracts or adds a noise reduction degree (the number of gradations) accepted from the user by the noise reduction degree setting accepting device 52 of the input acceptance/image display section 5 to or from the difference image generated by the difference calculating device 36, to generate a noise reduction processed image. In this manner, the accuracy in defect detection and the visibility of the difference image can be improved.

The highlighting processing device 38 multiplies the noise reduction processed image generated by the noise reduction processing device 37 by a gain (magnification) accepted from the user by the gain setting accepting device 53 of the input acceptance/image display section 5, to thereby generate a highlighting processed image. In this manner, the accuracy in defect detection and the visibility of the difference image can be improved. Furthermore, a combination of the noise reduction processing device 37 and the highlighting processing device 38 enables simplification and stabilization of the analysis even when executing separate image processing in a later stage.

The difference image selecting device 39 selects at least one difference image of the positive difference image and the negative difference image, that are subjected to noise reduction processing and highlighting processing by the noise reduction processing device 37 and the highlighting processing device 38, in accordance with the selection of the difference image accepted from the user by the difference image selection accepting device 54 of the input acceptance/image display section 5.

Figure 2:
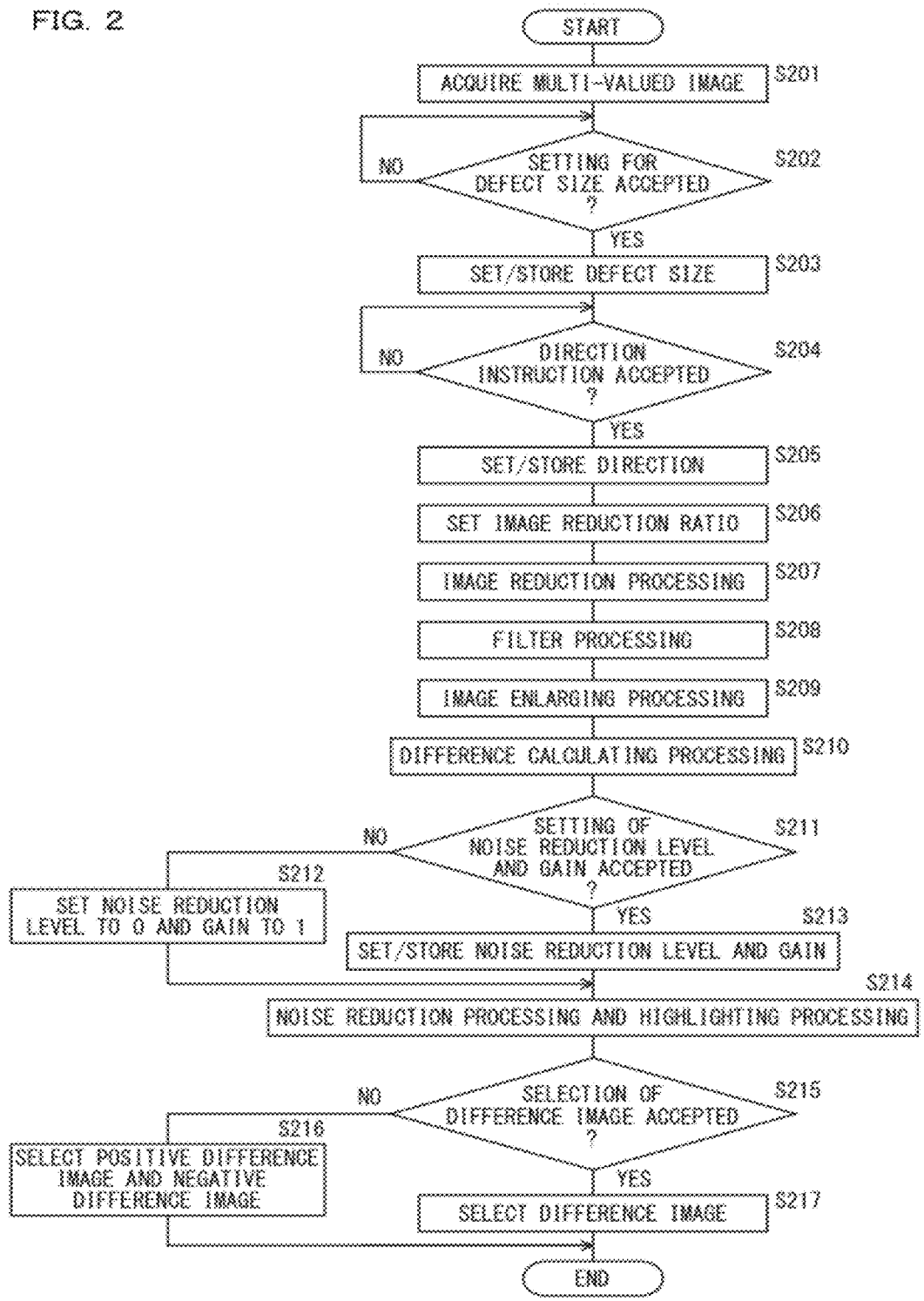
FIG. 2 is a flowchart showing the calculating processing steps for set data in a defect detection method using the defect detection apparatus according to the first embodiment of the present invention.

FIG. 2 is a flowchart showing each processing process of a defect detection method which is used in the defect detection apparatus 1 according to the first embodiment of the present invention. Each calculation processing step of the defect detection method according to the present invention is executed in accordance with a computer program according to the present invention which is stored in an inner portion of the image processing section 3.

In FIG. 2, firstly, the image processing section 3 acquires a multi-valued image of an object surface by image-capture (step S201). Next, the image processing section 3 determines whether or not the input acceptance/image display section 5 has accepted a setting of a defect size (pixel number) made by the user (step S202). When the image processing section 3 determines that the setting for the size of the defect has not been accepted (step S202: NO), the image processing section 3 adopts an acceptance standby state for the setting of the defect size. When the image processing section 3 determines that the setting for the size of the defect has been accepted (step S202: YES), the image processing section 3 sets and stores a defect size (step S203).

Next, the image processing section 3 determines whether or not the input acceptance/image display section 5 has accepted an instruction for the direction of image processing (step S204). When the image processing section 3 determines that the input acceptance/image display section 5 has not accepted an instruction for the direction (step S204: NO), the image processing section 3 adopts an acceptance standby state for the direction instruction. When the image processing section 3 determines that the input acceptance/image display section 5 has accepted an instruction for the direction (step S204: YES), the image processing section 3 sets and stores the direction of image processing.

Next, the image processing section 3 sets an image reduction ratio in response to the stored defect size (step S206), and reduces the acquired multi-value image in the stored direction with the set image reduction ratio to thereby generate a reduced image (step S207). Then the image processing section 3 performs the filter processing in the stored direction on the reduced image in a filter size (or the number of times of passages through the filter) in accordance with the image reduction ratio (or defect size) (step S208).

It is necessary to remove a defect under consideration during performance of the image reduction processing and the filter processing. It is thereby possible to ultimately detect only the defect under consideration when a difference is created between the original multi-valued image and an image obtained by enlarging the reduced image (with the defect removed) to the size of the original multi-valued image.

A relation as expressed by Formula (1) exists between the size of a removable defect, the image reduction ratio, and the median filter size. That is to say, when the reduction ratio is denoted as 1/R and the median filter size is denoted as M, the size of the removable defect can be obtained using Formula (1). In Formula (1), RoundDown(x) means calculation by discarding the decimal point for x.

$$\text{RoundDown}(M/2) \times R \qquad (1)$$

Since the median filtering substitutes the pixel under examination by a median value for the intensity values of all pixels within a filter size range, a defect having a width of at least not larger than the filter size M, namely a width smaller than RoundDown(M/2), is substituted by a median value, and then removed. Furthermore, since median filtering is performed on the reduced image, the removed width is converted into a width on the original image, and thereby enables calculation of a size of the defect that can actually be removed. The width on the original image may be calculated by multiplying the width on the reduced image by the reciprocal of the enlargement ratio, and hence can be calculated using the formula as described above. For example, when the reduction ratio is set to 1/4 and the filter size is set to 5, the size of the removable defect is not larger than eight pixels.

Although an increase in the image reduction ratio enables performance of the processing at a higher speed, conversely, there is a tendency for the accuracy of shading image generation to be adversely affected due to higher image distortion. Further, as the filter size increases, even when the image reduction ratio is not very large (the image is not very distorted), the defect can be removed from the reduced image and the accuracy of the shading image can be maintained. However, conversely, the processing time tends to increase. Consequently, appropriate selection of the image reduction ratio and the filter size enables generation of a suitable reduced image with defects removed. These calculations may be retained in a configuration of a reference table with a defect size taken as an argument, or may be in the form of calculation on each occasion by use of a formula.

Next, the image processing section 3 enlarges the reduced image, subjected to the filter processing, in the stored direction at the image enlargement ratio R corresponding to the reciprocal of the image reduction ratio 1/R to thereby generate an enlarged image (shading image) (step S209). Next, the image processing section 3 performs a calculation of a difference between the original multi-valued image and the enlarged image to thereby generate a positive difference image (bright defect image) and negative difference image (dark defect image) as difference images (step S210).

Figure 3:
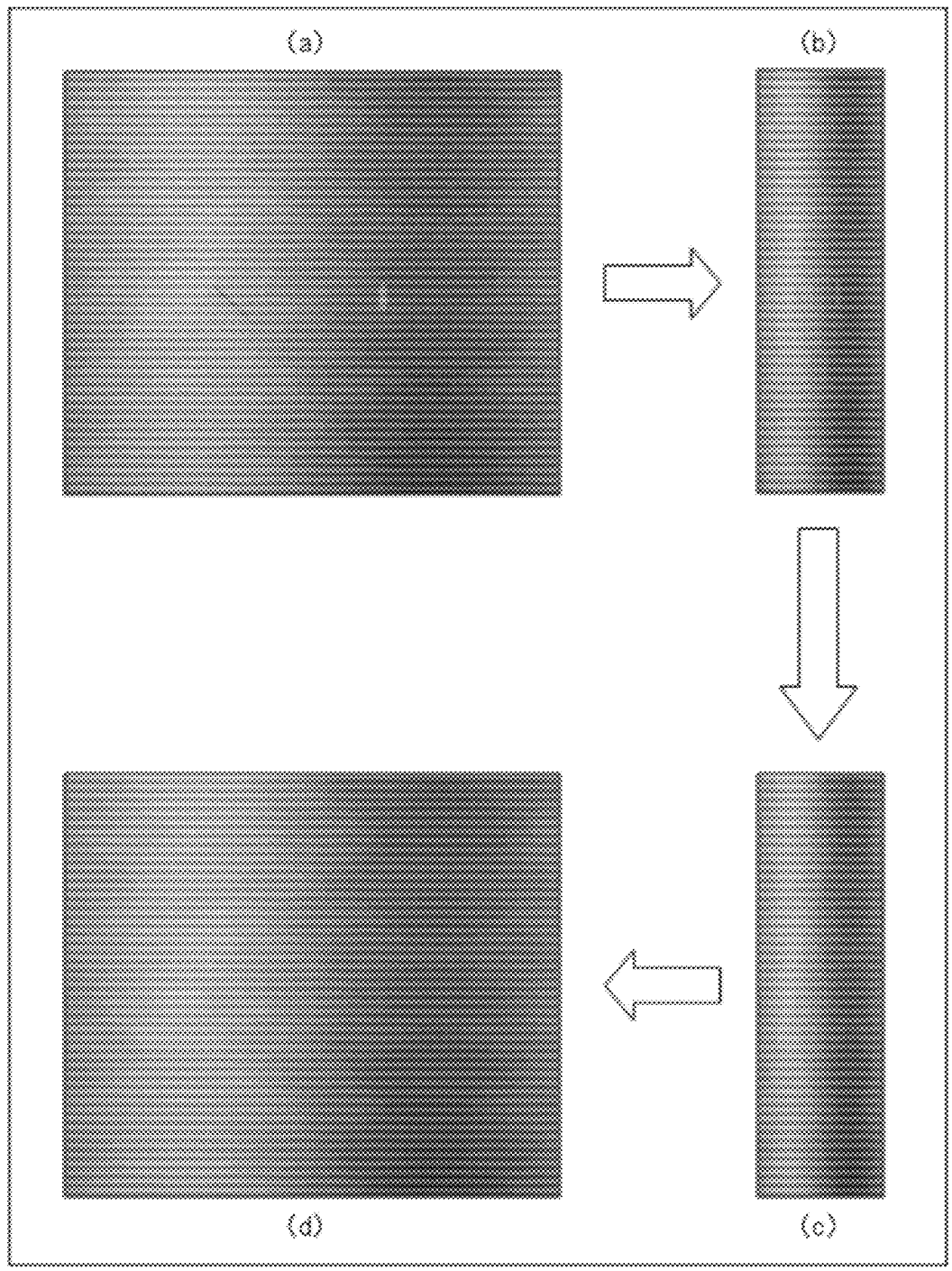
FIGS. 3(a)-(d) illustrate a transition of a multi-valued image when an instruction is received in an X direction in which the background pattern is uniformly continuous.

FIG. 3 illustrates the transition of a multi-valued image when an instruction is received in an X direction in which the background pattern is uniformly continuous. A background pattern that is uniformly continuous in the X direction is present in the multi-valued image illustrated in FIG. 3(a). FIG. 3(b) illustrates a reduced image when the multi-valued image is reduced by an image reduction ratio of 1/4 in the X direction. As illustrated in FIG. 3(b), the background pattern that is uniformly continuous in the X direction continues to be present and is not eliminated.

FIG. 3(c) illustrates a filter image when a filter process is applied in the X direction in relation to the reduced image. FIG. 3(d) illustrates an enlarged image (first enlarged image) when enlarging is executed in the X direction using an enlargement ratio 4 corresponding to the reciprocal of the image reduction ratio 1/4. Even when enlarged, the shading pattern and the background pattern that is uniformly continuous in the X direction continue to be present and are not eliminated.

Figure 4:
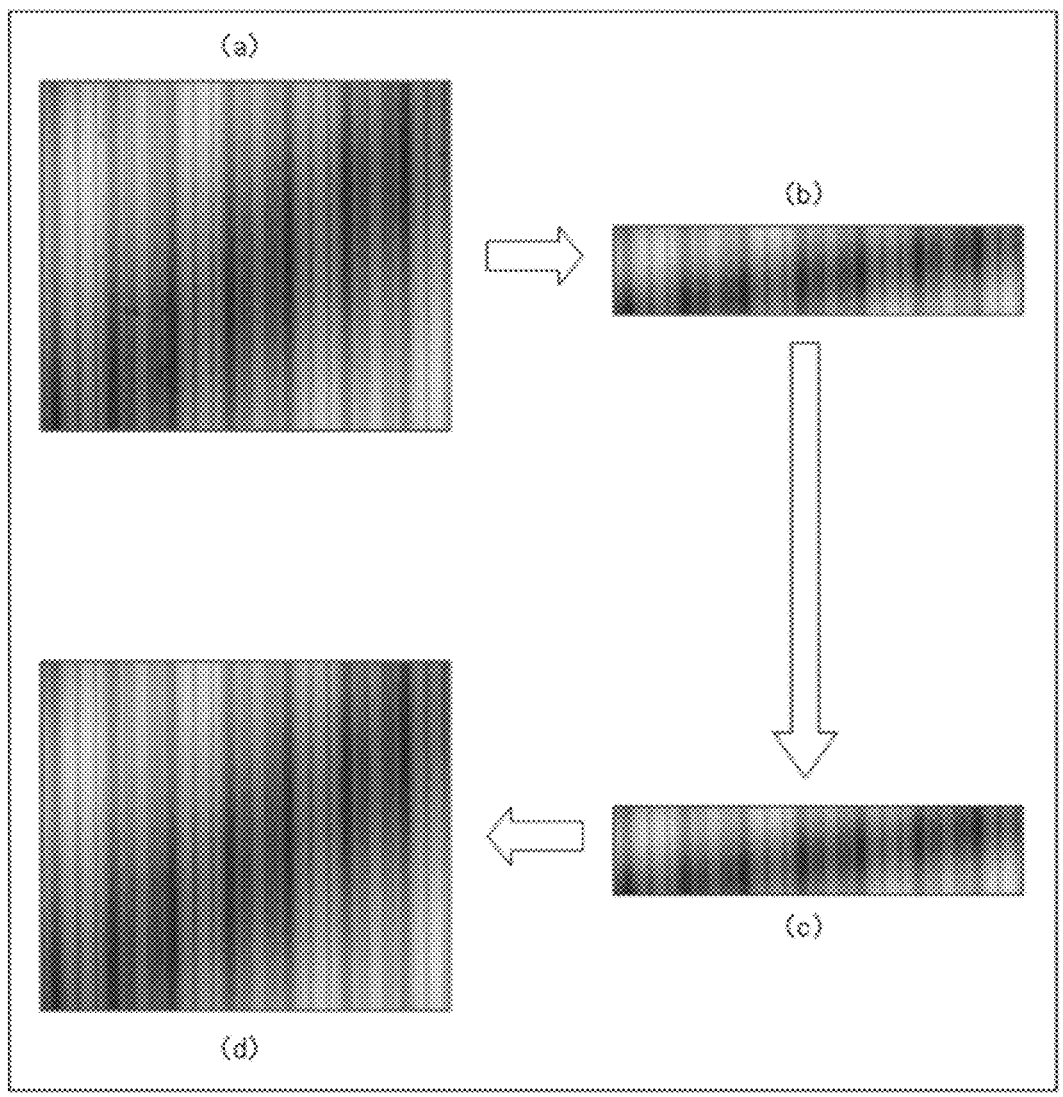
FIGS. 4(a)-(d) illustrate the transition of a multi-valued image when an instruction is received in a Y direction in which the background pattern is uniformly continuous.

FIG. 4 illustrates the transition of a multi-valued image when an instruction is received in a Y direction in which the background pattern is uniformly continuous. A background pattern that is uniformly continuous in the Y direction is present in the multi-valued image illustrated in FIG. 4(a). FIG. 4(b) illustrates a reduced image when the multi-valued image is reduced by an image reduction ratio of 1/4 in the Y direction. As illustrated in FIG. 4(b), the background pattern that is uniformly continuous in the Y direction continues to be present and is not eliminated.

FIG. 4(c) illustrates a filter image when a filter process is applied in the Y direction in relation to the reduced image. FIG. 4(d) illustrates an enlarged image (first enlarged image) when enlarging is executed in the Y direction using an enlargement ratio 4 corresponding to the reciprocal of the image reduction ratio 1/4. Even when enlarged, the shading pattern and the background pattern that is uniformly continuous in the Y direction continue to be present and are not eliminated.

Therefore, a difference image is generated by the calculation of a difference between the original multi-valued image and the enlarged image (first enlarged image) by the difference calculating unit 36 to thereby enable elimination of a background pattern that is uniformly continuous in the X direction or a background pattern that is uniformly continuous in the Y direction in addition to the shading pattern, and thus ensure detection of a defect.

Figure 5:
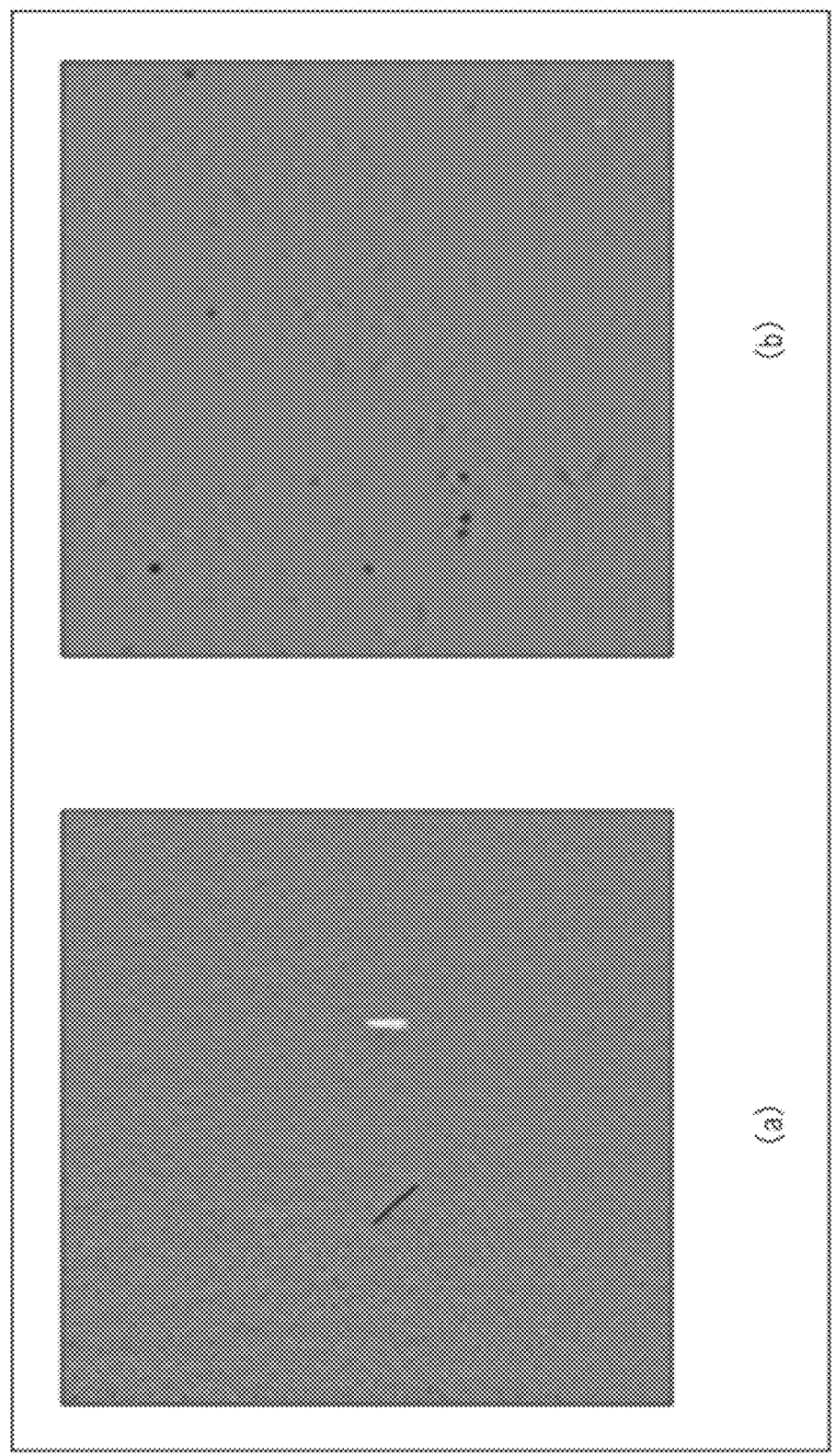
FIGS. 5(a) and (b) illustrate a difference image generated by execution of calculation of the difference between an original multi-valued image and an enlarged image.

FIG. 5 illustrates a difference image generated by execution of calculation of the difference between an original multi-valued image and an enlarged image. FIG. 5(a) illustrates a difference image based on the original multi-valued image illustrated in FIG. 3, and FIG. 5(b) illustrates a difference image based on the original multi-valued image illustrated in FIG. 4. Since there is a match between the shading pattern and the background pattern, in addition to the original multi-valued image and enlarged image (first enlarged image), the generation of the difference image enables detection of the differences being only the defects illustrated in FIG. 5(a) and FIG. 5(b). In FIG. 5(a) and FIG. 5(b), a value ±0 which is the boundary between positive and negative in the difference image is represented as an intermediate intensity value (gain).

Returning now to FIG. 2, the image processing section 3 determines whether or not a setting for a noise reduction degree (the number of gradations) and a gain (magnification) in the generated positive difference image and negative difference image has been accepted from the user (step S211). When the image processing section 3 determines that a setting for the noise reduction degree (the number of gradations) and the gain (magnification) has not been accepted (step S211: NO), the image processing section 3 sets the noise reduction degree to 0 as a default, and sets the gain to 1 (step S212). On the other hand, when the image processing section 3 determines that a setting for the noise reduction degree (the number of gradations) and the gain (magnification) has been accepted (step S211: YES), the image processing section 3 sets and stores a noise reduction degree and a gain of the accepted user settings (step S213).

Next, the image processing section 3 performs noise reduction processing and highlighting processing on the generated positive difference image and negative difference image by use of the stored noise reduction degree and gain (step S214). In this context, the noise reduction degree is denoted as N, the gain is denoted as G, and a difference value of the generated difference image is denoted as D (i, j) wherein (i, j) illustrates a coordinate position on the image. When the difference value after performance of the noise reduction processing and the highlighting processing is written as D'(i, j), the difference value D'(i, j) is given by Formula (2).

$$D'(i,j)=\text{Max}(D(i,j)-N,0).\text{times}.G \text{ (when } D(i,j) \text{ is positive)}$$

$$D'(i,j)=\text{Min}(D(i,j)+N,0).\text{times}.G \text{ (when } D(i,j) \text{ is negative)} \quad (2)$$

In Formula (2), Min(x, y) means a calculation for obtaining the smaller value of the values for "x" and "y".

Figure 6:
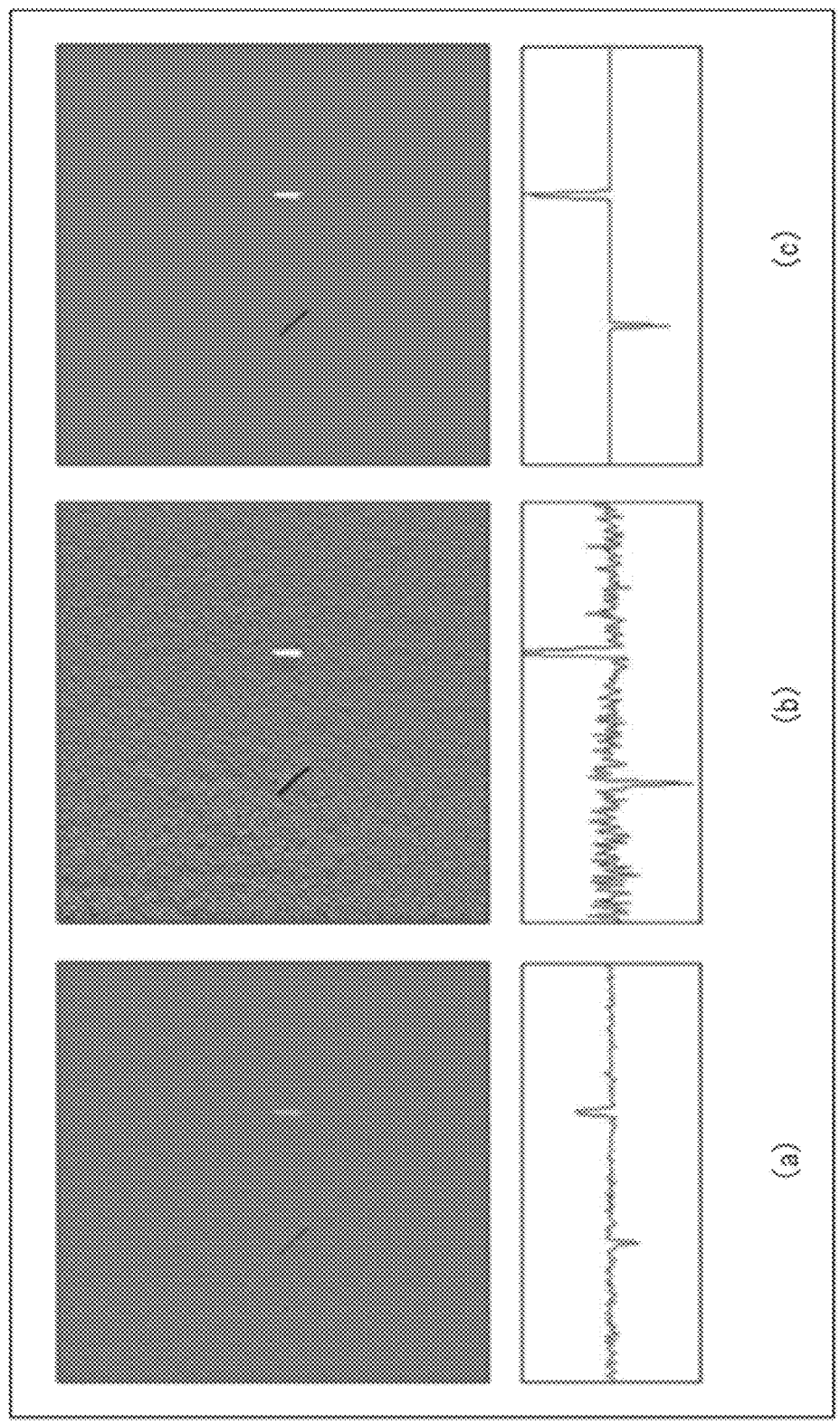
FIGS. 6(a)-(c) illustrate a difference image after execution of a noise reduction process and a highlighting process.

FIG. 6 illustrates a difference image after execution of a noise reduction process and a highlighting process. FIG. 6(a) illustrates the original multi-valued image and the intensity value profile illustrated in FIG. 3, FIG. 6(b) illustrates the difference image and the intensity value profile after execution of the highlighting process on the difference image based on the original multi-valued image illustrated in FIG. 3, and FIG. 6(c) illustrates the difference image and the intensity value profile after execution of the noise reduction process and the highlighting process on the difference image based on the original multi-valued image illustrated in FIG. 3.

FIG. 6(b) shows the gain G set to a value of 4, and the defect is thereby highlighted by approximately 4 times. In addition to a highlighting process in which the gain G set to a value of 4, FIG. 6(c) illustrates execution of a noise reduction processing in which the noise reduction level N is set to 20 to thereby effectively remove noise. Therefore, effective detection of only defects is enabled. Furthermore, the analysis can be simplified and stabilized even when executing separate image processing in a later stage.

Further, different noise reduction degrees and gains can be set in the positive difference image and the negative difference image. In this manner, when there are different allowable values for a defect, the user can freely make adjustments when for example, it is decided to increase the highlighting of one of the images. In this context, when the noise reduction degree is denoted as Nw and the gain is denoted as Gw with respect to the positive difference image, and the noise reduction degree is denoted as Nb and the gain is denoted as Gb with respect to the negative difference image, the difference value D'(i, j) after performance of the noise reduction processing and the highlighting processing is given by Formula (3).

$$D'(i,j)=\text{Max}(D(i,j)-Nw,0).\text{times}.Gw \text{ (when } D(i,j) \text{ is positive)}$$

$$D'(i,j)=\text{Min}(D(i,j)+Nb,0).\text{times}.Gb \text{ (when } D(i,j) \text{ is negative)} \quad (3)$$

Returning now to FIG. 2, the image processing section 3 determines whether or not a selection from a user of at least one difference image of the positive difference image and the negative difference image has been accepted (step S215), and when a selection of a difference image has not been accepted (step S215: NO), the image processing section 3 selects the positive difference image and the negative difference image as defaults (step S216), and completes the processing. On the other hand, when a selection of at least one difference image of the positive difference image and the negative difference image has been accepted (step S215: YES), the image processing section 3 selects the difference image for which a selection from a user has been accepted (step S217), and completes the processing.

When the image data is an eight-bit data and the result of the selecting processing is Z(i, j), the selection processing for the difference image is performed by a clipping calculation expressed by Formula (4).

$$Z(i,j)=\text{Clip}(D'(i,j),0,255) \text{ (when selecting the positive difference image)}$$

$$Z(i,j)=\text{Clip}(D'(i,j),+255,0,255) \text{ (when selecting the negative difference image)}$$

$$Z(i,j)=\text{Clip}(D'(i,j),+128,0,255) \text{ (when selecting both the positive and negative difference images)} \quad (4)$$

It should be noted that in Formula (4), Clip(n, x, y) means that "x" is selected when n<y, "y" is selected when n>y, and "n" is selected when x≤n≤y.

Figure 7:
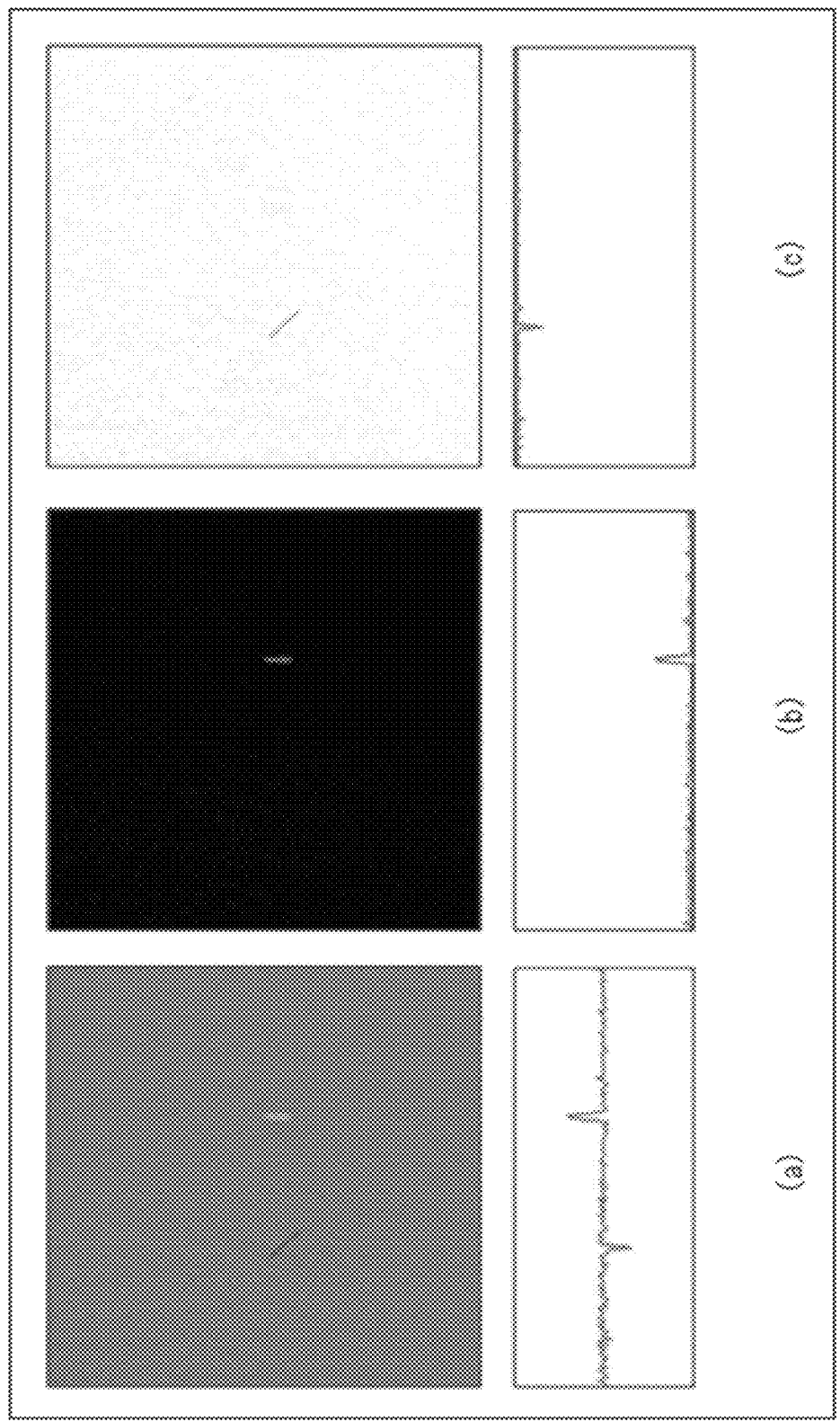
FIGS. 7(a)-(c) illustrate a difference image when selection is accepted in relation to at least one difference image of a positive difference image and a negative difference image.

FIG. 7 illustrates a difference image when a selection of at least one difference image of the positive difference image and the negative difference image has been accepted. FIG. 7(a) illustrates the difference image and the intensity value profile after selection of both the positive difference image and the negative difference image based on the original multi-valued image illustrated in FIG. 3, and FIG. 7(b) illustrates the difference image and the intensity value profile after selection of the positive difference image based on the original multi-valued image illustrated in FIG. 3, and FIG. 7(c) illustrates the difference image and the intensity value profile after selection of the negative difference image based on the original multi-valued image illustrated in FIG. 3.

As shown when comparing the intensity value profiles illustrated in FIGS. 7(a), (b) and (c), both the positive defects and negative defects can be detected in FIG. 7(a), whereas only the positive defects are detected in FIG. 7(b), and only the negative defects are detected in FIG. 7(c). Therefore, selection and screening of a defect to be the object of detection can be ensured.

As thus described, according to the present first embodiment, a difference image is repetitively acquired by variation of the defect size, the direction of image reduction processing, filter processing, and image reduction processing, the level of noise reduction, the gain, and the like until the difference image can be acquired that is desired by a user, that is to say, a difference image can be acquired in which only defects that are detected as defects by a user are separated from the background pattern, and displayed. The defect size, the direction of image reduction processing, filter processing, and image reduction processing, the level of noise reduction, the gain, and the like at the time that it is determined that the desired difference image has been acquired are stored as set data to thereby acquire a difference image for use in defect detection by use of the stored set data.

Figure 8:
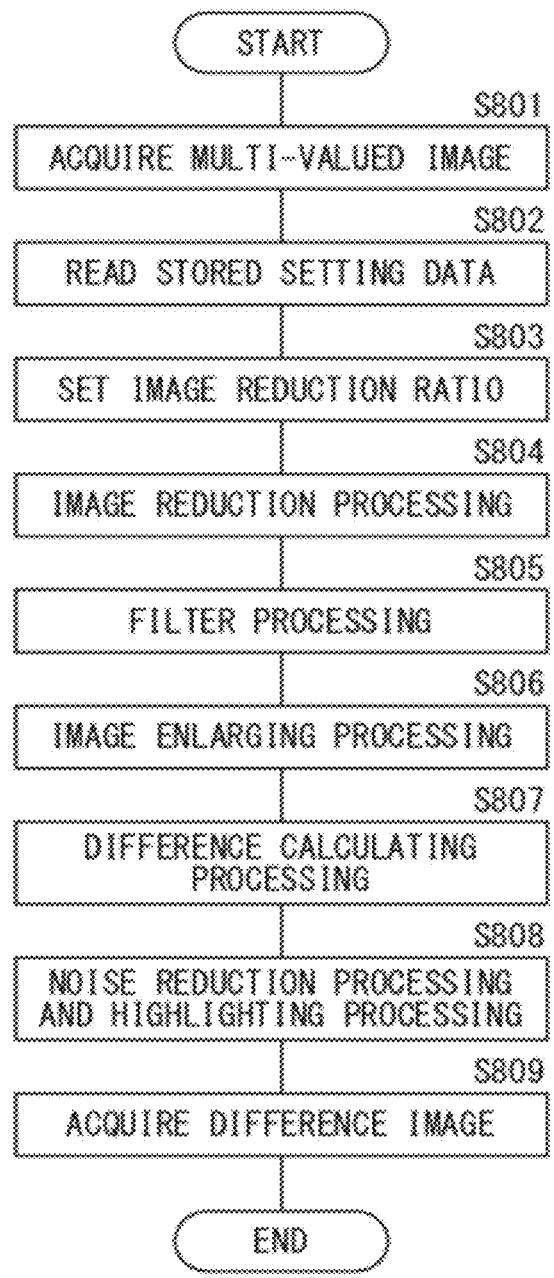
FIG. 8 is a flowchart showing the acquisition processing step for a difference image according to a defect detection method using the defect detection apparatus according to the first embodiment of the present invention.

FIG. 8 is a flowchart showing the acquisition processing step for a difference image according to a defect detection method using the defect detection apparatus according to the first embodiment of the present invention. The acquisition processing step for a difference image according to a defect detection method of the present invention is executed according to a computer program according to the present invention that is stored in an inner portion of the image processing section 3.

The difference image that is acquired by the processing in FIG. 8 is an image for the object of a defect detection process. For example, the presence or absence of a defect, the position, and the like are determined by execution of an edge detection process for example, in relation to the acquired difference image. That is to say, the acquisition process of the difference image according to the first embodiment executes preprocessing to raise only the defects from the background pattern, and then a user can execute separate image processing in relation to the acquired difference image, and set determination reference values to thereby execute accurate determination and specification of the presence or absence of a defect, the position, and the like.

In FIG. 8, the image processing section 3 acquires a multi-valued image of an object surface by image-capture (step S801). Next, the image processing section 3 reads out the stored set data (step S802). More specifically, the defect size, the direction of image reduction processing, filter processing, and image reduction processing, the level of noise reduction, the gain, and the like are read out.

Next, the image processing section 3 sets an image reduction ratio in accordance with the read-out defect size (step S803), and reduces the acquired multi-valued image with the set image reduction ratio to generate a reduced image (step S804). Next, the image processing section 3 performs the filter processing in the stored direction on the reduced image in a filter size (or the number of times of passage through the filter) in accordance with the image reduction ratio (or defect size) (step S805).

Next, the image processing section 3 enlarges the reduced image, that has been subjected to the filter processing, in the direction of reading using the image enlargement ratio R corresponding to the reciprocal of the image reduction ratio 1/R to thereby generate an enlarged image (shading image) (step S806). Then, the image processing section 3 performs a calculation of a difference between the original multi-valued image and the enlarged image to thereby generate a positive difference image (bright defect image) and negative difference image (dark defect image) as difference images (step S807).

The image processing section 3 executes noise reduction processing and highlighting process based on the read-out noise reduction level and gain (step S808) to thereby acquire the desired difference image (step S809).

As thus described, according to the present first embodiment, without depending upon a change and a variation in generation state of shading included in a multi-valued image acquired by capture by the imaging device 2, since the multi-valued image is reduced only in a first direction in which the background pattern is uniformly continuous, a filter process is executed, and the image is enlarged to thereby generate a first enlarged image, a defect image of no more than a size set by a user can be removed from the reduced image. On the other hand, since the continuously uniform background pattern can be left without elimination from the reduced image, high accuracy detection of a defect of no more than the size desired by a user is possible by use of a difference image based on the original multi-valued image and the first enlarged image.

Second Embodiment

Figure 9:
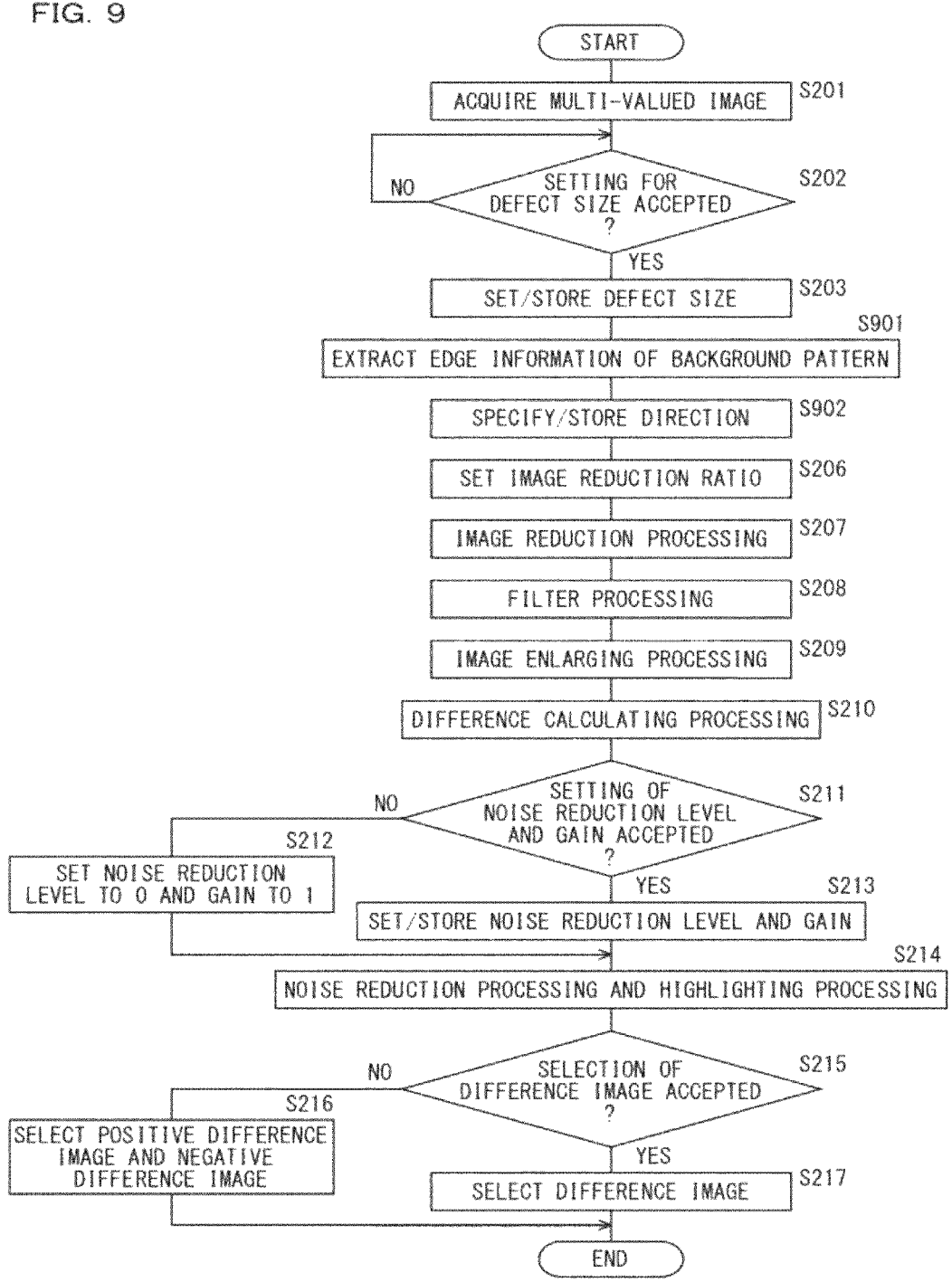
FIG. 9 is a flowchart showing the calculating processing steps for set data in a defect detection method using the defect detection apparatus according to a second embodiment of the present invention.

FIG. 9 is a flowchart showing the calculating processing steps for set data in a defect detection method using the defect detection apparatus according to the second embodiment of the present invention. The calculation processing of the set data in the defect detection method according to the present invention is executed according to a computer program according to the present invention that is stored in an inner portion of the image processing section 3. Those aspects of the processing flow in FIG. 9 that are subjected to the same processing as in FIG. 2 are denoted by the same reference numerals, and detailed description will not be repeated.

In FIG. 9, after the image processing section 3 sets and stores a defect size (step S203), the image processing section 3 extracts edge information for the background pattern (step S901). The second embodiment is also configured so that edge information is extracted as an edge in a constant direction due to the presence of the continuously uniform background pattern.

Next, the image processing section 3 specifies and stores the direction of execution of the image reduction process, the filter process and the image reduction process (first direction) based on the extracted edge information (step S902) (direction specifying device). In this manner, in the second embodiment, tracking and detection of a defect is enabled even when there is a change in the direction in which the background pattern is continuously uniform.

There is no particular limitation in relation to the filter used for extraction of edge information, and for example, a Sobel filter or the like may be used. An edge intensity and edge angle for each pixel configure the extracted edge information.

An angle histogram for the edge angle is generated in relation to a pixel that has an edge intensity that is greater than or equal to a predetermined value based on the extracted edge information. The edge angle that is the maximum value in the histogram is calculated to thereby specify the direction of execution of the image reduction process, the filter process, and the image enlarging process.

Of course, an inverse affine conversion may be applied to rotate the difference image to return to an original angle after the image is rotated using an affine conversion so that the calculated edge angle is in the Y direction (vertical direction) or the X direction (horizontal direction), and the image reducing process, the filter process, the image enlarging process, the difference image generation process, and the highlighting process and the like are executed in relation to the rotated image.

Third Embodiment

In the first and the second embodiment described above, although an enlarged image (first enlarged image) is generated to configure a basis for the difference image generation to detect a defect by reducing a multi-valued image, executing a filter process and then enlarging, an enlarged image (actually not enlarged) that configures a basis for the generation of a difference image may be generated by increasing the filter size or the number of times of passage through the filter without executing image reduction.

That is to say, the image reduction ratio is set to 1, and the filter processing device 34 may set the filter size or the number of times of passage through the filter in response to the size of the defect that is set and stored by the size setting and storing device 31. For example, a defect of a desired size can be detected by executing a filter process with a median filter in which the filter size is (S×2+1) relative to a size S for an extracted defect.

Figure 10:
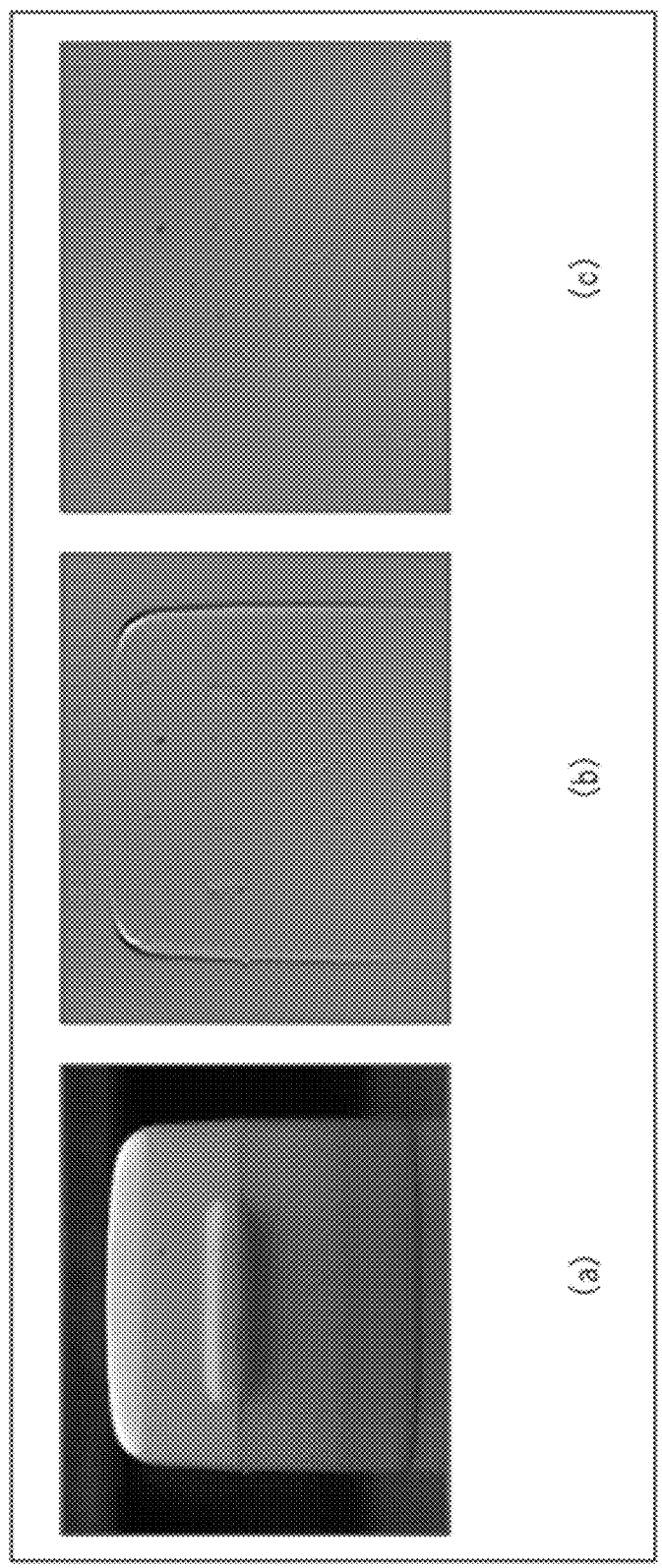
FIGS. 10(a)-(c) illustrate a difference image for defect extraction according to a defect detection method using the defect detection apparatus according to a third embodiment of the present invention.

FIG. 10 illustrates a difference image for defect extraction according to a defect detection method using the defect detection apparatus according to a third embodiment of the present invention. An instruction in the X direction is accepted in relation to the original multi-valued image illustrated in FIG. 10(a). FIG. 10(b) illustrates a difference image in which the image reduction ratio is set to 4 for example and the multi-valued image is reduced in the X direction, a filter process is executed, and the image is enlarged to thereby calculate the difference from the original multi-valued image. Since a pixel in which the intensity value has a large fluctuation range is detected, contour features between the background and the object for detection in the original multi-valued image are effectively detected as a defect.

In contrast, FIG. 10(c) illustrates a difference image in which the image reduction ratio is set to 1 to thereby execute a filter process without reducing and enlarging the multi-valued image, and then the difference from the original multi-valued image is calculated. Since the multi-valued image is not reduced and enlarged, although the filter processing time increases, effective removal of contour features of the background and detection object in the original multi-valued image is enabled by increasing the filter size or the number of times of passage through the filter, and therefore detection of only defects is ensured.

That is to say, when the size of the defect that is the object of detection is larger than a predetermined size, in the same manner as the first and the second embodiment, if a defect is detected by use of a difference image in which the multi-valued image is reduced in the direction for which an instruction has been accepted, a filter process is executed, and then the image is enlarged to thereby calculate the difference from the original multi-valued image, and the size of the defect being the object of detection is smaller than the predetermined value, in the same manner as the first and the second embodiment, the detection method may be changed in response to the size of the defect by executing filtering by increasing the filter size or the number of times of passage through the filter and detecting a defect from a difference image in which the difference from the original multi-valued image is calculated.

Further, since the filter size or the number of times of passage through the filter may be set in response to the size of the extracted defect, a user can effectively detect a defect by merely accepting an instruction in relation to the direction in which the background pattern is uniformly continuous and the size of the defect in the multi-valued image without reference to the image reduction ratio, the filter size, or the like.

Fourth Embodiment

The defect detection method according to the first embodiment or the second embodiment may be applied even when the uniformly continuous background pattern (continuous pattern) is present in two directions in addition to one direction. That is to say, firstly, an instruction is accepted in relation to a first direction (for example, the X direction), and in the same manner as the first embodiment, a reduced image is generated by reducing the original multi-valued image in the first direction using the set image reduction ratio, executing a filter process in the first direction on the reduced image to remove a defect in the reduced image, and generating a first enlarged image by enlarging the reduced image, that is subjected to the filter process, in the first direction using an image enlargement ratio that corresponds to the reciprocal of the image reduction ratio. Thereby a continuous pattern in the first direction can be removed by generating a difference image between the generated first enlarged image and the original multi-valued image.

Then, an instruction for a second direction (for example, the Y direction) is accepted, and in the same manner as the first embodiment, a reduced image is generated in which the generated difference image (the difference image of the first enlarged image and the multi-valued image) is reduced in the second direction using the set image reduction ratio. A filter processing is executed on the reduced image in the second direction for removing a defect from the reduced image to thereby produce a second enlarged image by enlarging the reduced image, subjected to filter processing, in the second direction with an image enlargement ratio that corresponds to the reciprocal of the image reduction ratio. Then, a second difference image between the second enlarged image and the first difference image (that is the difference image between the first enlarged image and the multi-valued image) is generated to thereby enable removal of the continuous pattern in the second direction in addition to the continuous pattern in the first direction.

That is to say, it is possible to remove a background pattern (continuous pattern) that is uniformly continuous in two directions can be removed by executing an image reducing process, a filter process, an image enlarging process and a difference image generating process continuously in two different directions. Even when there are three or more directions, obviously expansion is possible by simply increasing the processing in the same manner.

Figure 11:
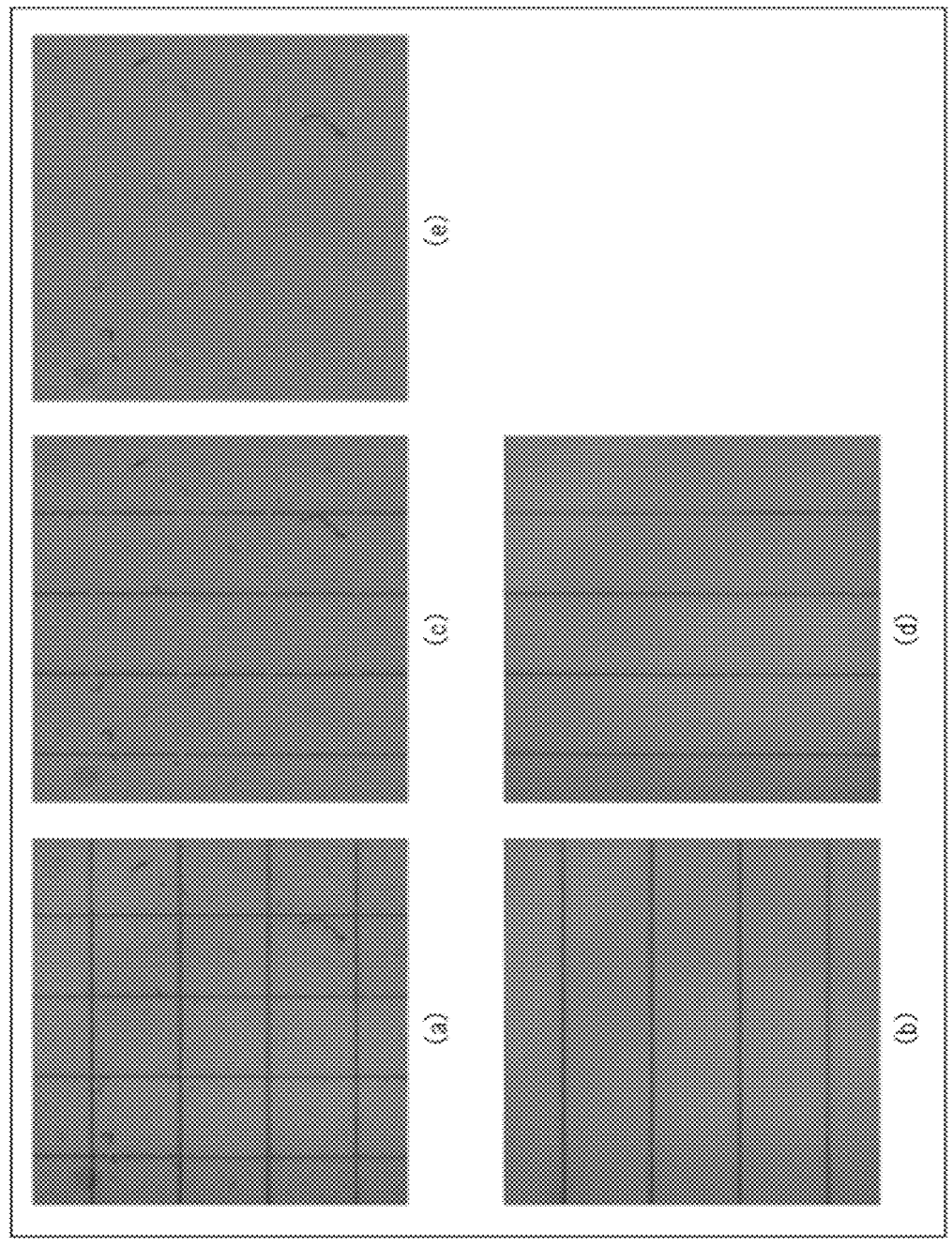
FIGS. 11(a)-(e) illustrate a difference image when executing an image reducing process, a filter process, an image enlarging process, and a difference image generating process continuously in the X direction and the Y direction in relation to a multi-valued image having a continuous pattern in the X direction and the Y direction.

FIG. 11 illustrates a difference image when executing an image reducing process, a filter process, an image enlarging process, and a difference image generating process continuously in the X direction and the Y direction in relation to a multi-valued image having a continuous pattern in the X direction and the Y direction. The multi-valued image illustrated in FIG. 11(a) includes a uniformly continuous background pattern (continuous pattern) that is present respectively in the X direction and the Y direction.

Firstly, an image reducing process, a filter process, and an image enlarging process are executed in relation to the original multi-valued image in the X direction to thereby generate an enlarged image (first enlarged image) as illustrated in FIG. 11(b). In FIG. 11(c), a difference image of the original multi-valued image in FIG. 11(a) and the enlarged image in FIG. 11(b) is generated. FIG. 11(c) illustrates the residual continuous pattern in the vertical direction although the continuous pattern in the transverse direction has been effectively removed.

Next, an image reducing process, a filter process, an image enlarging process are executed in the Y direction in relation to the difference image illustrated in FIG. 11(c) to thereby generate an enlarged image (second enlarged image) illustrated in FIG. 11(d). As illustrated in FIG. 11(e), a difference image (second difference image) of the difference image in FIG. 11(c) (first difference image) and the enlarged image in FIG. 11(d) is generated. FIG. 11(e) illustrates the detection of only defects, and the effective removal of the continuous pattern in the vertical direction in addition to the continuous pattern in the transverse direction.

Of course, there is no limitation to generating respective difference images in two different continuous directions, and a difference image may be generated by generation of a first enlarged image and a third enlarged image by performance of respective image reduction processing, filter processing and image enlarging process in a first direction and a second direction, that is different from the first direction, followed by calculation of the differences from the original multi-valued image based on a composite image of both those images.

That is to say, firstly, an instruction is accepted in relation to a first direction (for example, the X direction), and in the same manner as the first embodiment, a reduced image is generated by reducing the original multi-valued image in the first direction using the set image reduction ratio, and then a filter process for removing a defect in the reduced image is executed in the first direction in relation to the reduced image to thereby generate a first enlarged image in which the reduced image, that is subjected to the filter process, is enlarged in the first direction using an image enlargement ratio that corresponds to the reciprocal of the image reduction ratio.

Then, an instruction for a second direction (for example, the Y direction) is accepted, and in the same manner as the first embodiment, a reduced image is generated by reducing the original multi-valued image in the second direction using the set image reduction ratio, and then a filter process for removing a defect in the reduced image is executed in the second direction in relation to the reduced image to thereby generate a third enlarged image in which the reduced image, that is subjected to the filter process, is enlarged in the second direction using an image enlargement ratio that corresponds to the reciprocal of the image reduction ratio. The generation of a composite image by synthesizing the third enlarged image and the first enlarged image enables the generation of a composite image in which a background pattern that is uniformly continuous in the first direction and the second direction is present at the same position as the original multi-valued image.

Finally, since the continuous pattern in the first direction and the second direction is removed by generating a difference image in which the difference between the original multi-valued image and the composite image is calculated, detection of only defects is ensured.

Figure 12:
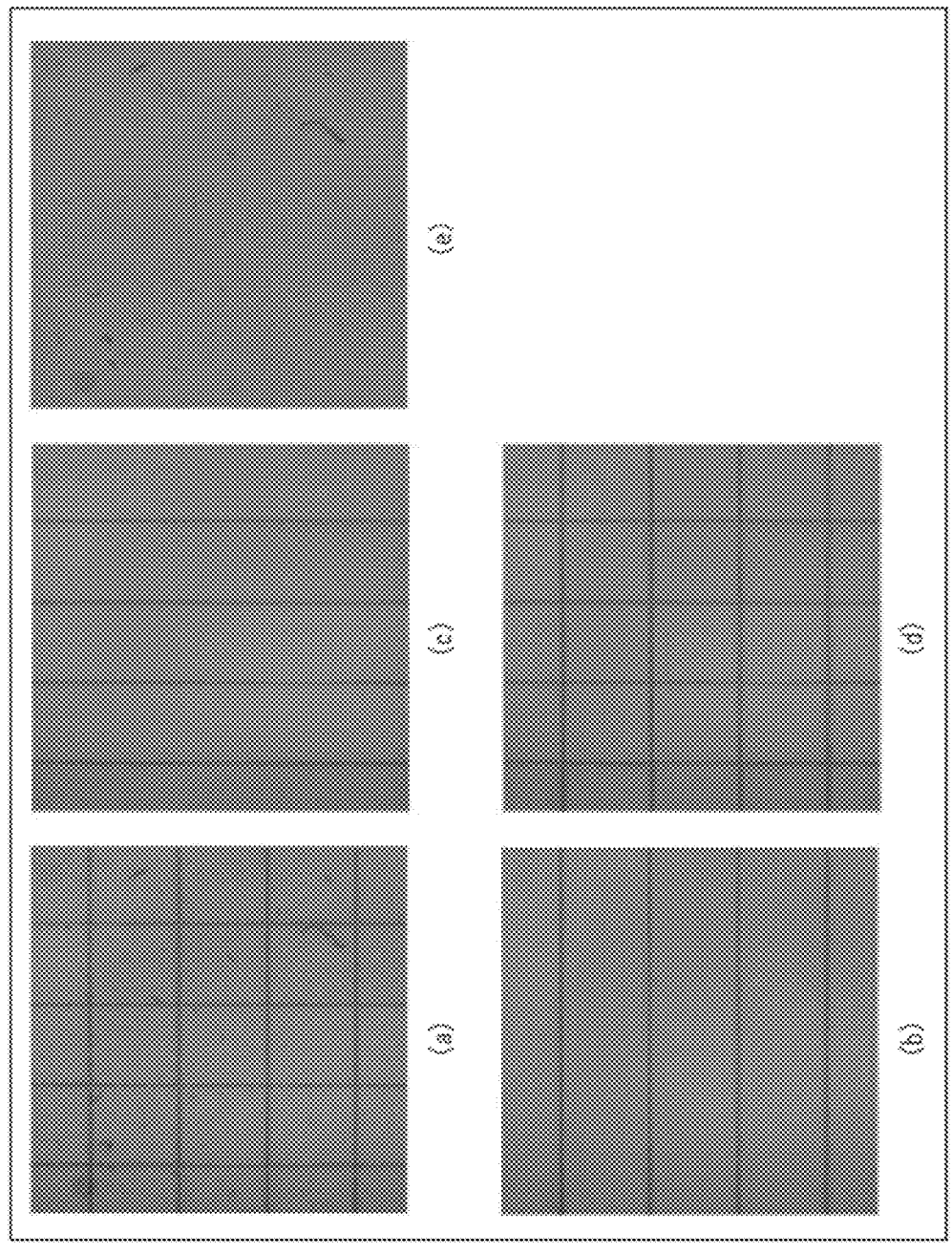
FIGS. 12(a)-(e) illustrate a difference image when a difference image is generated by separate execution of an image reducing process, a filter process, an image enlarging process in the X direction and the Y direction in relation to a multi-valued image having a continuous pattern in the X direction and the Y direction.

FIG. 12 illustrates a difference image when a difference image is generated by separate execution of an image reducing process, a filter process, an image enlarging process in the X direction and the Y direction in relation to a multi-valued image having a continuous pattern in the X direction and the Y direction. The original multi-valued image illustrated in FIG. 12(a) includes a continuously uniform background pattern (continuous pattern) respectively in the X direction and the Y direction.

Firstly, an image reducing process, a filter process, an image enlarging process are executed in the X direction in relation to the original multi-valued image to thereby generate an enlarged image (first enlarged image) illustrated in FIG. 12(b). Next, an image reducing process, a filter process, an image enlarging process are executed in the Y direction in relation to the original multi-valued image to thereby generate an enlarged image (third enlarged image) illustrated in FIG. 12(c).

Then, the enlarged image illustrated in FIG. 12(b) (first enlarged image) and the enlarged image that is illustrated in FIG. 12(c) (third enlarged image) are synthesized to thereby generate the composite image illustrated in FIG. 12(d). Whether smaller values for the intensity value are prioritized when generating the composite image by application of a so-called MIN calculation or whether larger values for the intensity value are prioritized by application of a so-called MAX calculation depends on the characteristics of the work and the defect. A MIN calculation has been applied in the example shown in FIG. 12.

Finally, a difference image of the original multi-valued image in FIG. 12(a) and the composite image in FIG. 12(d) is generated as shown in FIG. 12(e). In FIG. 12(e), a continuous pattern can be effectively removed in a vertical direction in addition to a continuous pattern in a transverse direction. Moreover, although this effect is difficult to discern from FIG. 11(e), there is no production of a white point (noise) with a higher intensity value than the peripheral portions, that tends to be produced as a side effect when executing difference processing on two occasions as a result of the intersection of the background pattern in the X direction and the background pattern in the Y direction. Moreover, since a single execution of the difference image generating process is sufficient, the calculation processing time can be shortened, and detection of only defects is enabled with a high accuracy. Even when there are three or more directions, obviously, expansion is possible by simply increasing the synthesized images in the same manner.

The present invention is not limited to the embodiments, and various variations and modifications may be made within the scope of the spirit of the invention. For example, although the first to the fourth embodiments were described using an a configuration using a medium filter as the filter processing device 34, the present invention is not limited in this respect, and an expansion filter or a compression filter may be used as long as there is a configuration that enables removal of a defect from a reduced image.

Further, the result of calculations by the difference calculating device 36 is not necessarily stored separately in the forms of the positive difference image and the negative difference image, but may be held as one difference image (for example, the images may be stored with a value .+-.0 as the boundary of the positive and the negative expressed as a median value of data). Moreover, the series of the image enlarging device 35, the difference calculating device 36, the noise reduction processing device 37, the highlighting processing device 38, and the difference image selecting device 39 is not necessarily performed such that the processing on a whole image is completed in each device and the process is then shifted to the next device, but the processing may be performed in pixel units in each device. That is, sequentially from a pixel on the left top of an image, the series of the image enlarging device (calculating the intensity value in a pixel under examination in an enlarged image) 35, the difference calculating device 36, the noise reduction processing device 37, the highlighting processing device 38, and the difference image selecting device 39 may be performed and a final result image may then be calculated.

EXPLANATION OF THE REFERENCE NUMERALS

1 DEFECT DETECTION APPARATUS
2 IMAGING DEVICE
3 IMAGE PROCESSING SECTION
4 STORING DEVICE
5 INPUT ACCEPTANCE/IMAGE DISPLAY SECTION
31 SIZE SETTING AND STORING DEVICE
32 REDUCTION RATIO SETTING DEVICE
33 IMAGE REDUCING DEVICE
34 FILTER PROCESSING DEVICE
35 IMAGE ENLARGING DEVICE
36 DIFFERENCE CALCULATING DEVICE
37 NOISE REDUCTION PROCESSING DEVICE
38 HIGHLIGHTING PROCESSING DEVICE
39 DIFFERENCE IMAGE SELECTING DEVICE
40 DIRECTION SETTING AND STORING DEVICE
41 IMAGE ROTATING DEVICE
51 SIZE SETTING ACCEPTING DEVICE
52 NOISE REDUCTION DEGREE SETTING ACCEPTING DEVICE
53 GAIN SETTING ACCEPTING DEVICE
54 DIFFERENCE IMAGE SELECTION ACCEPTING DEVICE
55 ORIGINAL IMAGE DISPLAYING DEVICE
56 ENLARGED IMAGE DISPLAYING DEVICE
57 DIFFERENCE IMAGE DISPLAYING DEVICE
58 DISPLAYED IMAGE SELECTION ACCEPTING DEVICE
59 DIRECTION INSTRUCTION ACCEPTING DEVICE

What is claimed is:

1. A defect detection apparatus for detecting a defect on an imaged object surface having a background pattern from a multi-valued image captured by an imaging device, the defect detection apparatus comprising:

a size setting and accepting device for accepting a setting of a size of a defect as a detection object;

a size storing device for storing the size of the defect for which the setting has been accepted by the size setting accepting device;

a direction instruction accepting device for accepting an instruction in relation to a first direction of the background pattern, wherein the background pattern has a uniformly continuous pattern in at least one direction;

a direction storing device for storing the first direction for which the instruction has been accepted by the direction instruction accepting device;

an image reducing device for generating a reduced image, the reduced image being reduced from the multi-valued image in the first direction of the background pattern, which is stored in the direction storing device and the reduced image being reduced such that a reduction ratio in the first direction is different from a reduction ratio in a second direction which is perpendicular to the first direction, with an image reduction ratio according to the size of the stored defect;

a filter processing device for performing filter processing in the first direction on the reduced image for removing a defect in the reduced image;

an image enlarging device for generating a first enlarged image obtained by enlarging the reduced image, subjected to the filter processing by the filter processing device, in the first direction with an image enlargement ratio corresponding to the reciprocal of the image reduction ratio; and a difference calculating device for generating a difference image by calculating a difference between the multi-valued image and the first enlarged image.

2. The defect detection apparatus according to claim 1, the defect detection apparatus further comprising:

a noise reduction degree setting accepting device for accepting a setting of a noise reduction degree in relation to the difference image generated by the difference calculating device; and a noise reduction processing device for adding or subtracting the accepted noise reduction degree to or from the difference image to thereby generate a noise reduction processing image.

3. The defect detection apparatus according to claim 1, the defect detection apparatus further comprising:

a gain setting accepting device for accepting a setting of a gain in relation to the difference image, and a highlighting processing device for multiplying the accepted gain by the difference image to thereby generate a highlighting processing image.

4. The defect detection apparatus according to claim 1, wherein the difference calculating device generates a positive difference image and a negative difference image; a difference image selection accepting device is provided for accepting a selection of at least one of the positive difference image and the negative difference image; and a difference image selecting device is provided for selecting the accepted difference image.

5. The defect detection apparatus according to claim 1, wherein the filter processing device is adapted to execute a setting so that the setting of a filter size or a number of times of passage through the filter increases as the size of the defect set by the size setting device increases.

6. The defect detection apparatus according to claim 1, the defect detection apparatus further comprising:

an edge information extracting device for extracting edge information of the background pattern; and a direction specifying device for specifying the first direction based on the extracted edge information.

7. The defect detection apparatus according to claim 6, the defect detection apparatus further comprising:

an image rotating device for rotating an image so that the specified first direction is the vertical direction or the horizontal direction.

8. The defect detection apparatus according to claim 1, wherein the image reduction ratio is set to 1, and the filter processing device sets the filter size or the number of times of passage through the filter in response to the size of the defect set by the size setting device.

9. The defect detection apparatus according to claim 1, wherein an instruction for a second direction, that is a different direction from the first direction, is accepted by the direction instruction accepting device; and the direction storing device also stores the second direction for which the instruction has been accepted by the direction instruction accepting device, the image reducing device generates a reduced image in which the difference image of the first enlarged image and the multi-valued image is reduced in the second direction using the image reduction ratio;

the filter processing device executes a filter processing in the second direction for removing a defect from the reduced image;

the image enlarging device produces a second enlarged image in the second direction by enlarging the reduced image, that is subjected to filter processing, with an image enlargement ratio that corresponds to the reciprocal of the image reduction ratio; and the difference calculating device generates a second difference image by calculating the difference between the second enlarged image and the first difference image that is the difference image between the first enlarged image and the multi-valued image.

10. The defect detection apparatus according to claim 9, wherein the image reducing device generates a reduced image by reducing the multi-valued image in the second direction with the image reduction ratio;

the filter processing device executes filter processing in the second direction to remove a defect from the reduced image;

the image enlarging device produces a third enlarged image by enlarging the reduced image, that is subjected to filter processing, in the second direction with an image enlargement ratio that corresponds to the reciprocal of the image reduction ratio; and the difference calculating device generates a difference image by calculating the difference between the multi-valued image and a composite image that synthesizes the first enlarged image and the third enlarged image.

11. A defect detection method used in a defect detection apparatus for detecting a defect on an imaged object surface having a background pattern from a multi-valued image captured by an imaging device, the method comprising the steps of:

accepting a setting of a size of a defect as a detection object;

storing the size of a defect for which a setting has been accepted in the size setting accepting step;

accepting an instruction in relation to a first direction of the background pattern, wherein the background pattern has a uniformly continuous pattern in at least one direction;

storing a first direction for which an instruction has been accepted in the direction instruction accepting step;

generating a reduced image which is reduced from the multi-valued image in the first direction of the background pattern with an image reduction ratio according to the size of the stored defect and the reduced image is reduced such that a reduction ratio in the first direction is different from a reduction ratio in a second direction which is perpendicular to the first direction;

executing filter processing in the first direction on the reduced image for removing a defect in the reduced image;

generating a first enlarged image obtained by enlarging the reduced image, subjected to the filter processing in the filter processing step, in the first direction with an image enlargement ratio corresponding to the reciprocal of the image reduction ratio; and generating a difference image obtained by calculating a difference between the multi-valued image and the first enlarged image.

12. A non-transitory computer program to be executed in the defect detection apparatus for detecting a defect on an imaged object surface having a background pattern from a multi-valued image captured by an imaging device, the computer program executing in the defect detection apparatus a size setting and accepting process for accepting a setting of a size of a defect as a detection object;

a size storing process for storing a size of a defect for which a setting has been accepted by the size setting accepting device;

a direction instruction accepting process for accepting an instruction in relation to a first direction of the background pattern, wherein the background pattern has a uniformly continuous pattern in at least one direction;

a direction storage process for storing the first direction for which an instruction has been accepted in the direction instruction accepting process;

an image reducing process for generating a reduced image, the reduced image being reduced from the multi-valued image in the first direction of the background pattern which is stored in the direction storing device, with an image reduction ratio according to the size of the stored defect, and the reduced image being reduced such that a reduction ratio in the first direction is different from a reduction ratio in a second direction which is perpendicular to the first direction;

a filter process for performing filter processing in the first direction on the reduced image for removing a defect in the reduced image;

an image enlarging process for generating a first enlarged image obtained by enlarging the reduced image, subjected to the filter processing by the filter processing device, in the first direction with an image enlargement ratio corresponding to the reciprocal of the image reduction ratio; and a difference calculating process for generating a difference image by calculating a difference between the multi-valued image and the first enlarged image.

13. The defect detection method according to claim 11, the method further comprising:

accepting a setting of a noise reduction degree in relation to the difference image; and adding or subtracting the accepted noise reduction degree to or from the difference image to thereby generate a noise reduction processing image.

14. The defect detection method according to claim 11, the method further comprising:

accepting a setting of a gain in relation to the difference image; and multiplying the accepted gain by the difference image to thereby generate a highlighting processing image.

15. The defect detection method according to claim 11, wherein generating the difference image is generating a positive difference image and a negative difference image, and the method further comprising:

accepting a selection of at least one of the positive difference image and the negative difference image; and selecting the accepted difference image.

16. The defect detection method according to claim 11, the method further comprising:

extracting edge information of the background pattern; and specifying the first direction based on the extracted edge information.

17. The computer program according to claim 12, the computer program further comprising:

a noise reduction degree setting accepting process for accepting a setting of a noise reduction degree in relation to the difference image generated by the difference calculating process; and a noise reduction processing process for adding or subtracting the accepted noise reduction degree to or from the difference image to thereby generate a noise reduction processing image.

18. The computer program according to claim 12, the computer program further comprising:

a gain setting accepting process for accepting a setting of a gain in relation to the difference image, and a highlighting processing process for multiplying the accepted gain by the difference image to thereby generate a highlighting processing image.

19. The computer program according to claim 12, wherein the difference calculating process generates a positive difference image and a negative difference image; and the computer program further comprising:

a difference image selection accepting process is provided for accepting a selection of at least one of the positive difference image and the negative difference image; and a difference image selecting process is provided for selecting the accepted difference image.

20. The computer program according to claim 12, the computer program further comprising:

an edge information extracting process for extracting edge information of the background pattern; and a direction specifying process for specifying the first direction based on the extracted edge information.

* * * * *